(12) United States Patent
Aeschlimann et al.

(10) Patent No.: US 8,403,938 B2
(45) Date of Patent: Mar. 26, 2013

(54) METHOD AND DEVICE FOR PRODUCING AN ANCHORAGE IN HUMAN OR ANIMAL TISSUE

(75) Inventors: Marcel Aeschlimann, Ligerz (CH); Laurent Torriani, Lamboing (CH); Mario Lehmann, Les Pommerats (CH); Jörg Mayer, Niederlenz (CH); Richard Lum, San Jose, CA (US); Kyle Craig Pilgeram, San Jose, CA (US); Michael Baycura, San Francisco, CA (US); Lisa Ballou, Santa Clara, CA (US)

(73) Assignees: Woodwelding AG, Stansstad (CH); Stryker Trauma GmbH, Schönkirchen/Keil (DE)

( * ) Notice: Subject to any disclaimer, the term of this patent is extended or adjusted under 35 U.S.C. 154(b) by 1112 days.

(21) Appl. No.: 12/260,698

(22) Filed: Oct. 29, 2008

(65) Prior Publication Data

US 2009/0131947 A1    May 21, 2009

Related U.S. Application Data

(60) Provisional application No. 60/983,791, filed on Oct. 30, 2007.

(51) Int. Cl.
*A61B 17/58* (2006.01)
(52) U.S. Cl. .......................................................... 606/93
(58) Field of Classification Search .................. 606/60, 606/86 R, 92–95, 99, 300, 304, 329, 331, 606/76, 77; 623/17.12, 23.58, 23.59, 23.62
See application file for complete search history.

(56) References Cited

U.S. PATENT DOCUMENTS

| | | | |
|---|---|---|---|
| 6,056,751 A * | 5/2000 | Fenton, Jr. ........................ 606/28 |
| 2003/0225438 A1 * | 12/2003 | Bonutti et al. ................ 606/232 |
| 2004/0030341 A1 * | 2/2004 | Aeschlimann et al. ......... 606/72 |
| 2005/0126680 A1 * | 6/2005 | Aeschlimann et al. ...... 156/73.1 |

FOREIGN PATENT DOCUMENTS

| | | |
|---|---|---|
| WO | 02/069817 A1 | 9/2002 |
| WO | 2008/034277 A2 | 3/2008 |

\* cited by examiner

*Primary Examiner* — Andrew Yang
*Assistant Examiner* — Diana S Jones
(74) *Attorney, Agent, or Firm* — Rankin, Hill & Clark LLP

(57) ABSTRACT

An anchorage in tissue is produced by holding a vibrating element and a counter element against each other such that their contact faces are in contact with each other, wherein at least one of the contact faces comprises a thermoplastic material which is liquefiable by mechanical vibration. While holding and then moving the two elements against each other, the vibrating element is vibrated and due to the vibration the thermoplastic material is liquefied between the contract faces, and due to the relative movement is made to flow from between the contact faces and to penetrate tissue located adjacent to outer edges of the contact faces. For liquefaction of the thermoplastic material and for displacing it from between the contact faces no force needs to act on the tissue surface which is to be penetrated by the liquefied material. For this reason anchorage in tissue which has little mechanical stability is possible.

16 Claims, 8 Drawing Sheets

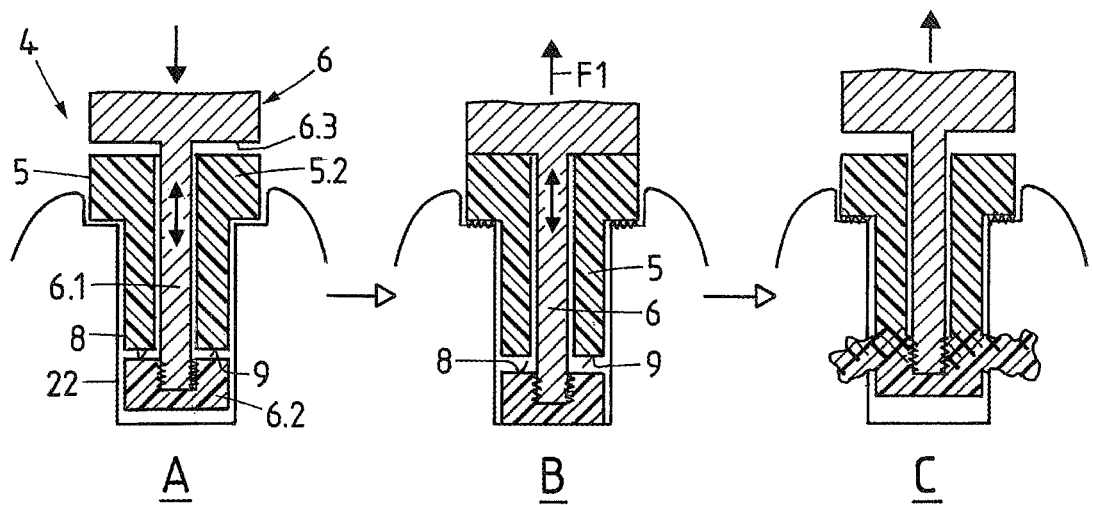
Fig. 5
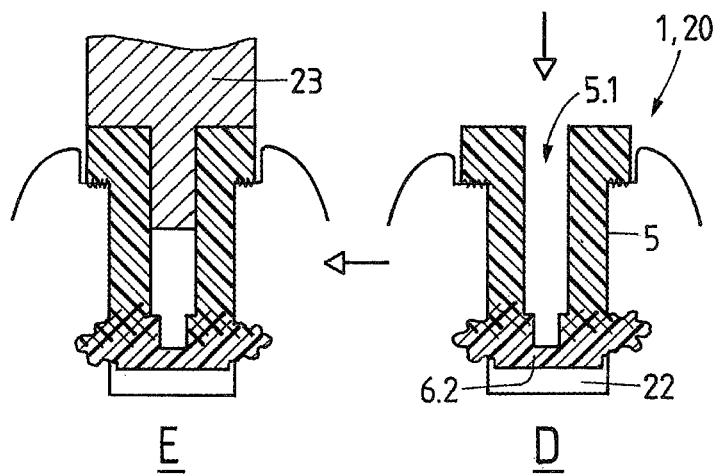
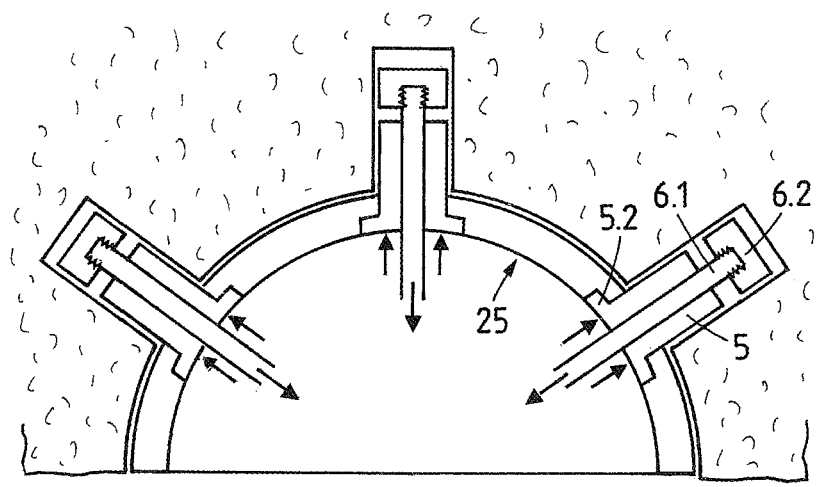
Fig. 6

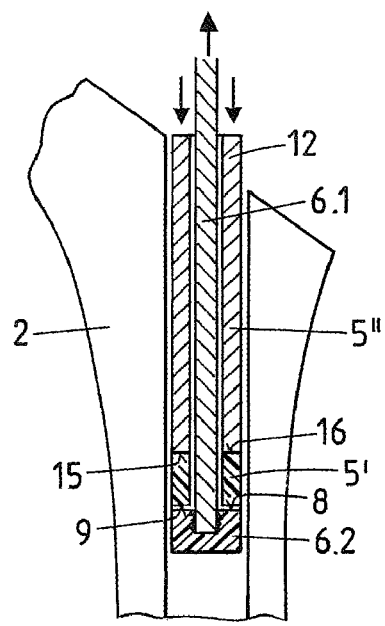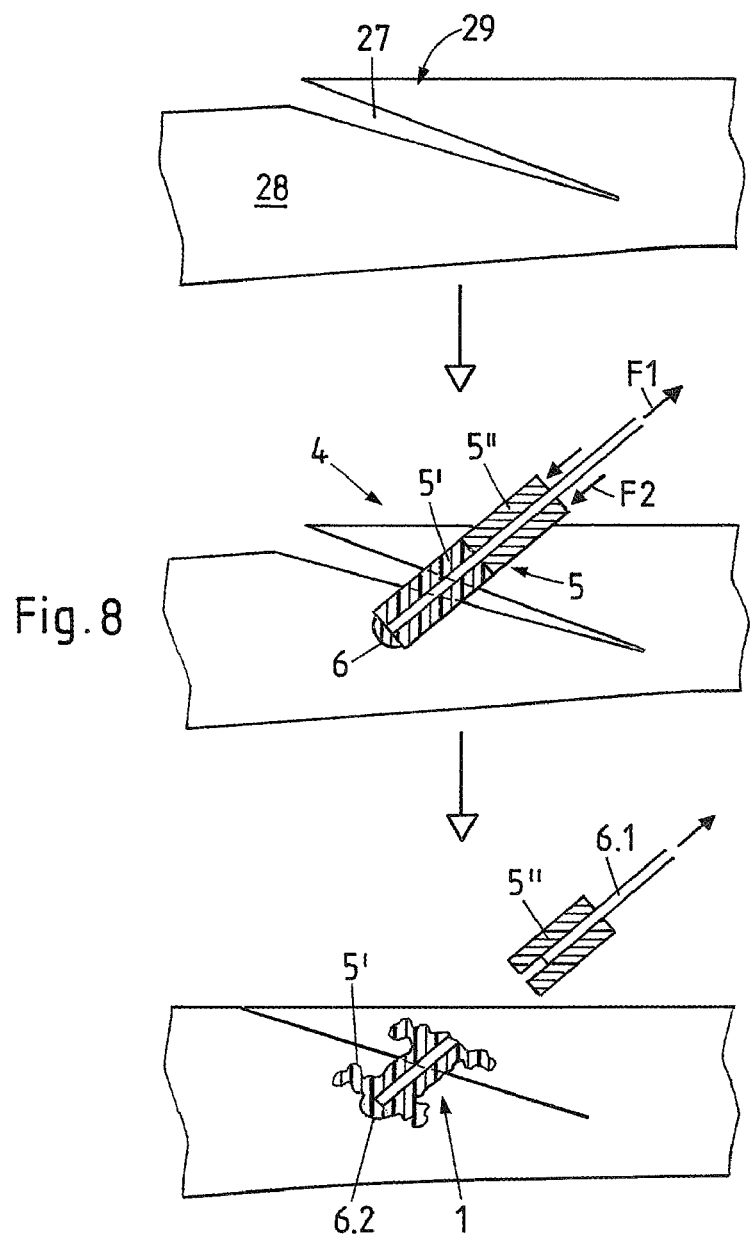

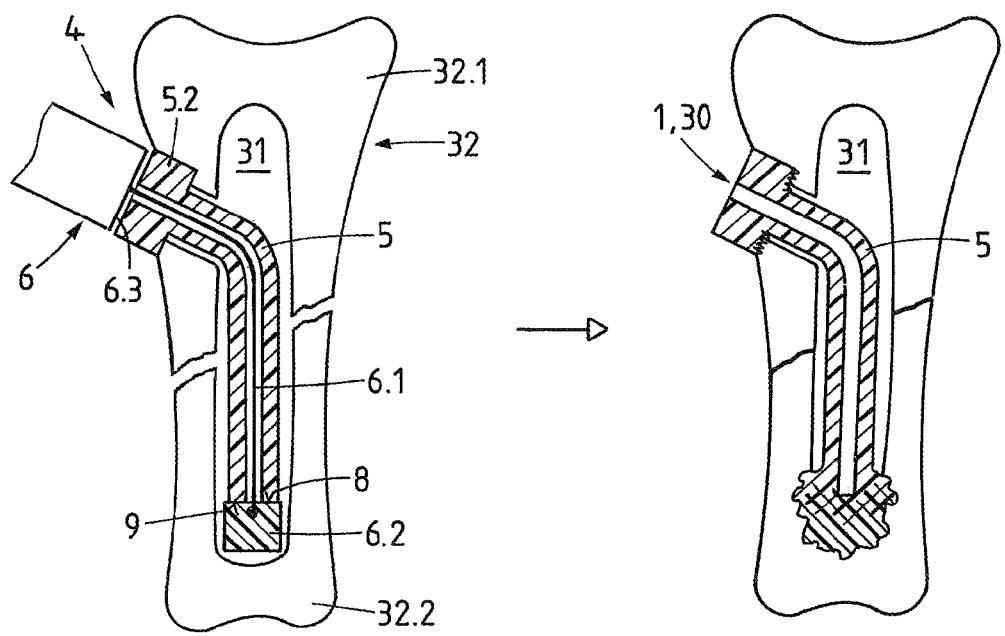
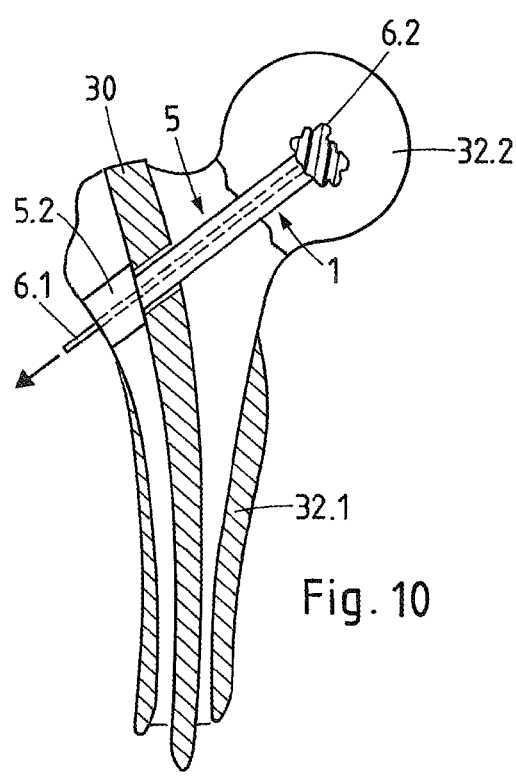
Fig. 10
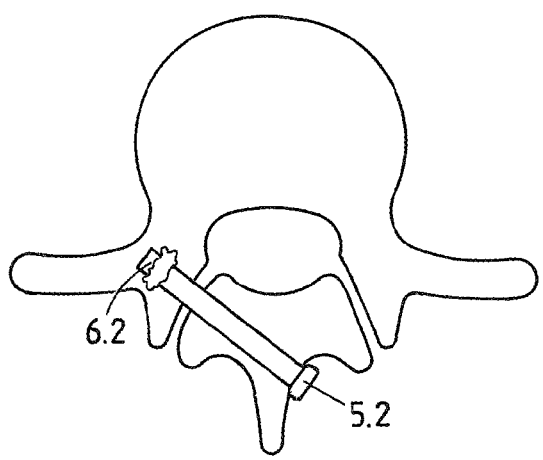
Fig. 11

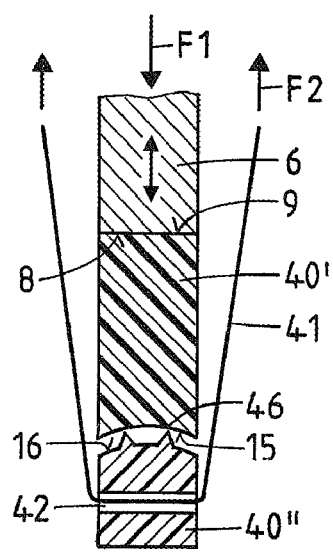
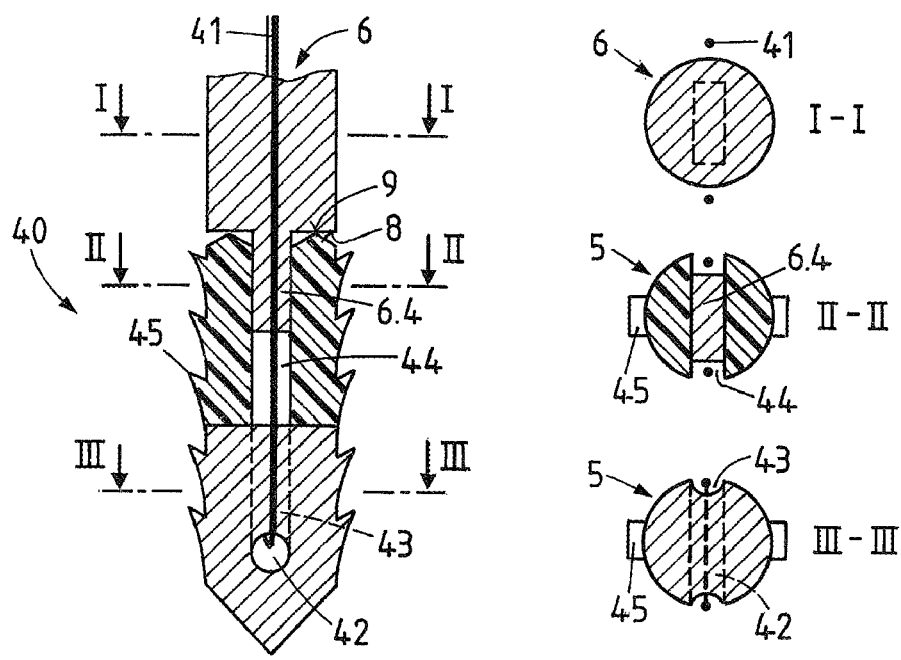
Fig. 18
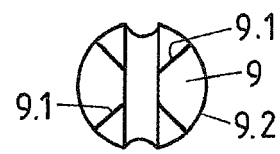
Fig. 19
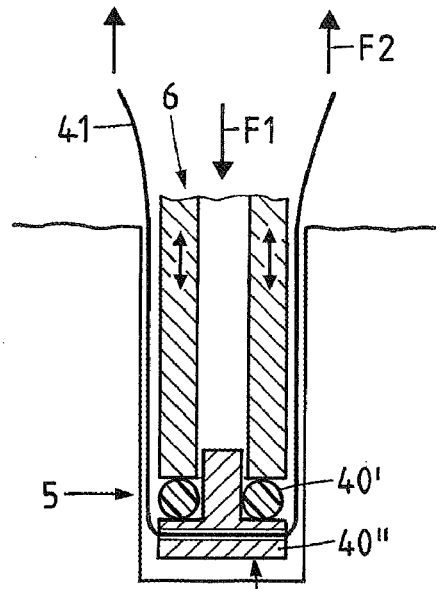
Fig. 20

METHOD AND DEVICE FOR PRODUCING AN ANCHORAGE IN HUMAN OR ANIMAL TISSUE

The claimed invention was made on behalf of parties to joint research agreements, which were in effect before the date of the claimed invention. The claimed invention was made as a result of activities within the scope of the joint research agreements. The parties of the joint research agreements are Stryker Endoscopy, US, Stryker Trauma GmbH & Co. KG, Germany, Woodwelding AG, Switzerland, and WW-Technology AG, Switzerland.

BACKGROUND OF THE INVENTION

Field of the Invention

The invention is in the field of medical implants and concerns a method for producing an anchorage in human or animal tissue wherein the tissue is a load-bearing tissue and the anchorage is achieved by creating a positive fit connection to the tissue, the connection having load bearing capability and being created with the aid of mechanical vibration and a thermoplastic material which is liquefiable by the mechanical vibration. The invention further concerns a device which is suitable for carrying out the method according to the invention. The load bearing tissue in which the implant is anchored is e.g. bone, cartilage, tendon, ligament or meniscal tissue and it is in particular a tissue which is capable of comparatively only little mechanical resistance (against mechanical vibration), such as e.g. cancellous bone tissue or osteoporotic bone tissue.

The publication WO 02/069817 and the presently unpublished international application No. PCT/CH2007/000459 by Woodwelding AG concern anchorage of an implant in bone tissue with the aid of mechanical vibration and a thermoplastic material which is liquefiable by the mechanical vibration, i.e. the thermoplastic material is capable of being liquefied when vibrated and simultaneously kept in contact with a non-vibrating hard bone surface. According to the named patent applications, the implant comprises the thermoplastic material at surfaces which are to be in contact with the bone tissue and the implant is pressed against the bone tissue and simultaneously contacted with a vibrating tool (e.g. sonotrode of an ultrasonic device). The thermoplastic material, where in contact with the bone tissue, is liquefied and pressed into pores or cavities of the bone tissue to constitute, when re-solidified, a positive fit connection with the bone tissue.

According to this state of the art, the pressing force is applied by the sonotrode to a proximal end of the implant while e.g. a distal end and/or a shoulder thereof is pressed against the bone tissue (bone surface, step in opening provided in bone tissue or bottom of such opening), resulting in liquefaction and therewith anchorage predominantly at the distal element end. The implant can also be pushed or pulled with the aid of the sonotrode into a bone opening of a slightly smaller cross section, such that pressure builds up between the implant and the bone tissue of the lateral wall of the opening, which results in liquefaction on lateral sides of the implant and therewith lateral anchorage. Lateral anchorage can also be achieved with elements which are compressible in the direction in which the sonotrode acts and, due to such compression, get larger perpendicular to the named direction. If such an element is compressed when positioned in a correspondingly dimensioned opening in the bone tissue, there is again a pressure build-up between the element and the bone tissue of the lateral wall of the opening and, on application of the vibration to the compressed element, anchorage is effected in this wall. Therein it is suggested to achieve the compression of the implant either between the sonotrode and the bone tissue (e.g. bottom of the opening) or between the sonotrode and a counter element.

In all methods according to the named state of the art, a pressure is built up between the implant and the bone tissue, in which anchorage is desired, which pressure enables liquefaction of the thermoplastic material and is believed to enable penetration of the liquefied material into the bone tissue. For enabling such pressure build-up, the bone tissue needs to have a minimum mechanical strength, i.e. liquefaction by pressing against softer tissues than bone is hardly possible. Furthermore, method parameters need to be adapted to the mechanical strength of a specific bone tissue in which anchorage is to be achieved.

BRIEF SUMMARY OF THE INVENTION

It is the object of the invention to create a further method for producing an anchorage in tissue with the aid of mechanical vibration and a thermoplastic material, which is liquefiable by the mechanical vibration, wherein the anchorage is again achieved by liquefying the thermoplastic material through the mechanical vibration and by penetration of pores, openings or cavities in the tissue such that, on re-solidification, the thermoplastic material constitutes a positive fit connection with the tissue. Other than the known methods, the method according to the invention is to be applicable not only with tissue of the mechanical strength or resistance required for the named liquefaction by the known methods but also with tissue with less mechanical strength or resistance and it is to necessitate no or at least considerably less adaptation to the mechanical characteristics of the tissue in which the anchorage is to be produced. This means in particular that the method according to the invention is to be applicable for less dense bone tissue (in particular cancellous bone tissue of little density or highly osteoporotic bone tissue) than the known methods and also for load-bearing tissues other than bone, such as e.g. tendon, ligament, cartilage or meniscal tissue.

The principal idea on which the inventive method is based, is to come away from liquefaction of the thermoplastic material between a vibrating implant and the (non-vibrating) bone tissue. Instead liquefaction is achieved between a vibrating element and a counter element which elements are positioned adjacent to the tissue and held against each other. The vibrating element is connected to a vibration source while the counter element is substantially non-vibrating or may be vibrating differently from the vibrating element such that in any case there is a relative vibratory movement between contact faces of the two elements which relative movement causes liquefaction of the liquefiable material which is arranged on at least one of the contact faces of the elements. The material being liquefied between the two elements is made to flow out from between the two elements by moving the two elements against each other, and it penetrates the adjacent tissue. Therein the two elements are arranged such that the force necessary for holding and moving them against each other is not acting on the tissue which is to be penetrated by the liquefied material. This means that, for the named liquefaction and penetration, the only force acting on the tissue, in which anchorage is achieved, is the hydrostatic pressure of the liquefied material. Experiments show that tissue such as cancellous bone tissue puts very little resistance against penetration by the liquefied material and therefore very little hydrostatic pressure will build up and act on the tissue and therefore damage to the tissue is at a minimum.

In soft tissue of non-porous nature the hydrostatic pressure of the liquefied material will displace tissue sections relative to other tissue sections, thus creating room for the liquefied material in situ, and, on re-solidification, the anchorage through the desired positive-fit connection.

The thermoplastic material to be liquefied between the vibrating element and the counter element is arranged on the vibrating and/or on the counter element in the area of a contact face at which the two elements are in contact with each other when the elements are held and moved against each other. Depending on which one of the two elements comprises the liquefiable thermoplastic material it will be the counter element or a part thereof or the vibrating element or a part thereof or a combination of the two which will remain in the tissue and constitute the anchored implant. In an implant of more than one part it is possible to form a joint between the parts substantially simultaneously with the anchoring process.

For enabling the liquefied material to flow from between the two elements and to come into contact with the tissue for penetration thereof, the vibrating element and the counter element held against each other are positioned relative to the tissue such that a surface of the tissue extends across outer edges of the contact faces and, in the region of these outer edges is in contact with the elements or slightly distanced therefrom, but preferably without the elements being pressed against the tissue surface at least in the area of the named outer edges of the contact faces.

The vibrating element is designed as a mechanically stable resonator suitable for transmitting mechanical vibration from a proximal end to a distal end with as little damping loss as possible, wherein the vibration has e.g. a direction predominantly parallel to an axis extending between the proximal and the distal end of the vibrating element, but may also be a rotational or radial vibration or a combination thereof. The proximal end of the vibrating element is equipped for being attached directly or indirectly to a source of the mechanical vibration (e.g. piezoelectric transducer) in a manner such that the vibration of the vibration source is transmitted to the vibrating element. The distal end of the vibrating element comprises the contact face which faces away from or towards the proximal end of the vibrating element, is adapted to the contact face of the counter element, and may comprise the liquefiable thermoplastic material. The vibrating element is preferably a one-part element which may comprise portions of different materials which portions are rigidly fixed to each other (e.g. by screwing, gluing or welding). However, it is possible also to use a two-part or even multi-part vibrating element wherein a most proximal part is attached to the vibration source and further parts are held against the most proximal part and against each other such that the vibration of the vibration source or at least part thereof is able to be transmitted through all the parts to a most distal part of the vibrating element which comprises the contact face at which liquefaction is to take place.

The counter element has a contact end which carries a contact face and an opposite end. The counter element is a one-part element which may comprise portions of different materials, which portions are rigidly connected to each other, but it may also comprise two or more than two parts which are not connected to each other. Such non-connected parts of the counter element include further contact faces adapted to each other. Between such further contact faces of parts of the counter element further liquefaction may occur, if at least one contact face of a pair of further contact faces includes a further liquefiable thermoplastic material. Two-point or multi-point anchorage can be achieved with such further liquefaction. However, due to poor vibration transmission from the vibrating element to the counter element between which liquefaction occurs, such further liquefaction will usually be considerably less pronounced than the liquefaction at the contact face of the vibrating element.

The counter element will usually be non-vibrating or vibrating only to a degree in which vibration transmission is possible through the contact faces between the vibrating element and the counter element where liquefaction occurs. However, as previously mentioned it is possible also to couple the counter element to a further vibration source (or via a transmission element to the same vibration source or even to the vibrating element), wherein the two vibration sources are operated such that there is a relative vibratory movement between the contact face of the vibrating element and the contact face of the counter element. This can be achieved by e.g. a difference in vibration direction, a difference in vibration frequency and/or a phase difference.

Preferably, but not necessarily, the vibrating element and the counter element comprise an axis each, the axis of the vibrating element extending between the proximal end and the distal end of the vibrating element and the axis of the counter element extending between the contact end and the opposite end of the counter element. The contact faces are arranged around the corresponding axis and non-parallel thereto. For holding and moving the elements against each other with the contact faces in contact with each other, the axis of the vibration element is aligned with the axis of the counter element and holding forces or at least components thereof act in the direction of the aligned axes.

If the contact face of the vibrating element faces away from the proximal end of the vibrating element, the counter element (or at least a region thereof) is held in a position beyond the distal end of the vibrating element (further distal than the distal end of the vibrating element). If the contact face of the vibrating element faces towards the proximal end of the vibrating element, the counter element (or at least a region thereof) is positioned between the distal and the proximal end of the vibrating element, wherein the vibrating element reaches through or past the counter element.

The above mentioned holding forces are applied actively to one of the elements each, or one of the holding forces is applied actively to one of the elements and is counteracted by the other element being supported against a support element which has e.g. a fixed position relative to the tissue. Depending on the named support, one or both elements will be moved relative to the tissue in which anchorage is to be achieved. For applying the opposite holding forces, it is possible also to use a pre-tensioned resilient connector between e.g. a non-vibrating support of the vibrating element (e.g. housing of the vibration source) and the counter element, the resilient connector biasing the two elements against each other.

Anchorage according to the invention is preferably effected in a bore or other opening provided in the tissue, wherein the opening can be provided in a preliminary method step or, in particular in soft tissue, can be produced by insertion of the implant elements. Advantageously, the holding forces are applied from one side of the tissue only, preferably from the side at which the vibration source is positioned (proximal side). This is easily achieved for a vibrating element with a contact face facing towards its proximal end and extending through or past a counter element being arranged between the distal and the proximal end of the vibrating element. For a vibrating element with a contact face facing away from its proximal end and the counter element being positioned beyond the distal end of the vibrating element, application of the two holding forces from the proximal side of the tissue becomes possible if the counter element extends in a proximal direction through or past at least the distal end of the vibrating element.

As mentioned above, at least one of the vibrating or the counter element comprises the thermoplastic material which is to be liquefied between the elements. For controlled liquefaction at the contact faces, the elements need to have a considerable stiffness and, therefore, contrary to the teaching of the above named international patent application, the elements, whether comprising the liquefiable thermoplastic material or not, are in a solid state, substantially non-compressible in the direction of their axes and therefore, their extension perpendicular to these axes will remain substantially the same (enlargement at the most 2%) under the influence of the above discussed holding forces. The holding forces needed for holding and moving the elements against each other can usually be as low as about 5N per mm2 area of material contact face (measured perpendicular to the axis), but may also be greater.

The device according to the invention, which device is suitable for carrying out the method according to the invention, comprises the vibrating element and the counter element and may further comprise the vibration source (e.g. ultrasonic transducer comprising a piezoelectric element) to which the vibrating element is connected and on which the counter element may be supported such that the device constitutes a load frame. Alternatively the device may comprise a hand piece with a housing and within the housing a releasable connection between the vibrating part and a cable through which the vibration is transmitted from a stationary vibration source to the vibrating element.

The vibrating element and the counter element have e.g. at least in the area of the contact faces a similar cylindrical form (circular cylinder or cylinder of any other cross section), wherein the contact faces extend around the cylinder axes and e.g. perpendicular to the axes (not parallel thereto) and comprise outer edges around the cylinder circumference. The elements are held against each other with aligned axes and at least the area of the contact faces is positioned in a bore or other opening in the tissue wherein the bore or opening has a cross section adapted to the elements such that on introduction of the elements in the bore or opening no pressure builds up between lateral walls of the bore or opening and the elements, i.e. the opening or bore has a cross section which is preferably somewhat larger than the cross section of the elements. Therein it is no condition for the invention that the shape of the two contact faces is the same or that the cross section of the vibrating element and of the counter element in the region of the contact faces is the same. Different such shapes and cross sections are possible also.

Mechanical vibration or oscillation suitable for the method according to the invention has preferably a frequency between 2 and 200 kHz (even more preferably between 10 and 100 kHz, or between 20 and 40 kHz) and a vibration energy of 0.2 to 20 W per square millimeter of active surface. The vibrating element is e.g. designed such that its contact face oscillates predominantly in the direction of the element axis (longitudinal vibration) and with an amplitude of between 1 and 100 µm, preferably around 10 to 20 µm. Rotative or radial oscillation is possible also.

In this text the expression "thermoplastic material being liquefiable by mechanical vibration" or in short "liquefiable thermoplastic material" or "liquefiable material" is used for describing a material including at least one thermoplastic component, which material becomes liquid or flowable when arranged at one of a pair of surfaces (contact faces) being in contact with each other and vibrationally moved relative to each other, wherein the frequency of the vibration is between 2 kHz and 200 kHz, preferably 20 to 40 kHz and the amplitude between 1 µm and 100 µm, preferably around 10 to 20 µm. Such vibrations are e.g. produced by ultrasonic devices as e.g. known for dental applications. For being able to constitute a load-bearing connection to the tissue, the material has an elasticity coefficient of more than 0.5 GPa, preferably more than 1 Gpa and a plastification temperature of up to 200° C., of between 200° C. and 300° C. or of even more than 300° C. Depending on the application, the liquefiable thermoplastic material may or may not be resorbable.

Suitable non-resorbable thermoplastic materials are, each of medical quality, polyolefins (e.g. polyethylene), polyacrylates, polymethacrylates, polycarbonates, polyamides, polyesters, polyurethanes, polysulfones, liquid crystal polymers (LCPs), polyacetals, halogenated polymers, in particular halogenated polyolefins, polyphenylene sulphones, polysulfones, polyarylether ketones (e.g. polyether etherketone PEEK), polyethers, or corresponding copolymers and/or blended polymers and/or composites of such polymers, in particular polyamide 11 or polyamide 12.

Suitable resorbable thermoplastic materials are, each of medical quality, thermoplastic polymers based on lactic and/or glycolic acid (PLA, PLLA, PGA, PLGA etc.) or polyhydroxy-alkanoates (PHA), polycaprolactones (PCL), polysaccharides, polydioxanons (PD), polyanhydrides, polypeptides, trimethyl-carbonates (TMC), or corresponding copolymers and/or blended polymers and/or composites of such polymers. Especially suitable as resorbable thermoplastic materials are poly-LDL-lactides (e.g. available from Böhringer under the commercial name Resomer LR706) or poly-DL-lactides (e.g. available from Böhringer under the commercial name Resomer R208).

In addition to one or a plurality of the above listed thermoplastic components, the liquefiable thermoplastic material may also include non-liquefiable components, such as reinforcing fibers, reinforcing splints, filling materials etc. which are evenly distributed in the thermoplastic component or are present in locally varying concentrations.

In the present text the expression "non-liquefiable material" is used for describing a material which is not liquefied under implantation conditions. Such a material is e.g. a metal (e.g. steel, titanium, titanium alloy, cobalt/chromium alloy), a ceramic or glass-like material (e.g. aluminum oxide, zirconium oxide, ceramic or glass of calcium phosphate), or a thermoset polymer.

If the vibrating element and the counter element of the device according to the invention comprise two different liquefiable thermoplastic materials at their contact faces (or at further contact faces between parts of a multi-part counter element), then both thermoplastic materials may be liquefied. This is not the case, if one of the two thermoplastic materials has a melting temperature or glass transition temperature respectively which is at least 50° C. higher than the corresponding temperature of the other material. The higher melting thermoplastic material is in such a case "non-liquefiable". However, the same thermoplastic material may be the liquefiable material in a different system in which it is located at a contact face and is the lowest melting material of the system. For preventing liquefaction in unwanted locations, e.g. between not connected parts of the vibrating element and/or of the counter element in which a thermoplastic material needs to be present for different reasons, care is to be taken that the difference in melting temperature between the thermoplastic material which is to be liquefied and the one which is not to be liquefied is at least 50° C.

An example of a pair of thermoplastic materials usable in the above manner consists of PEEK (non-liquefiable) and PLLA (liquefiable). On the other hand, in a pair of PEEK and titanium, PEEK is the liquefiable material. Further high-temperature thermoplastic materials which can assume the part of a non-liquefiable material in a device according to the invention are e.g. polyether arylketones, polyfluoro- or polychloroethylenes, polyether imides, polyether sulphones, polyvinylchloride, polyurethanes, polysulphones, polyesters or composite materials (e.g. high-temperature thermoplastic reinforced with carbon fibers).

BRIEF DESCRIPTION OF THE DRAWINGS

The invention is further described with the aid of exemplary embodiments of the method and the device, which are illustrated in the appended Figs., wherein:

FIG. 5 illustrates a further exemplary embodiment of the invention concerning anchorage of a stem-like implant, e.g. dental implant, wherein the counter element is located between the distal and the proximal end of the vibrating element, which reaches through the counter element, wherein the liquefiable thermoplastic material is comprised by both the vibrating and the counter element, and wherein the produced implant is constituted by the counter element and an end piece of the vibrating element;

FIG. 6 shows the embodiment according to FIG. 5 applied for anchoring a resurfacing prosthesis, e.g. a casing for the bearing part of a joint prosthesis;

FIG. 7 shows the embodiment according to FIG. 5 applied for sealing the marrow space of a tubular bone or bone cavity, e.g. for producing a cement stopper;

FIG. 8 shows the application of the method according to FIG. 5 to soft tissue, e.g. meniscal tissue;

FIGS. 9 to 11 illustrate the embodiment according to FIG. 5, concerning fixation of two tissue fragments or parts relative to each other, wherein the method further comprises a step of anchoring a distal end piece of the vibrating element in bone tissue and the produced implant is able to function in a similar manner as a tension screw;

FIGS. 17 and 18 show a further exemplary embodiment of the invention applied for anchoring a suture in tissue, wherein the contact face of the vibrating element faces away from its proximal end and the counter element is arranged beyond the distal end of the vibrating element and through the suture reaches past the latter, wherein the liquefiable thermoplastic material is comprised by the counter element, and wherein the produced implant is constituted by the counter element only;

FIGS. 19 to 21 show further embodiments similar to the embodiment according to FIGS. 17 and 18;

DETAILED DESCRIPTION OF THE INVENTION

Figure 1:
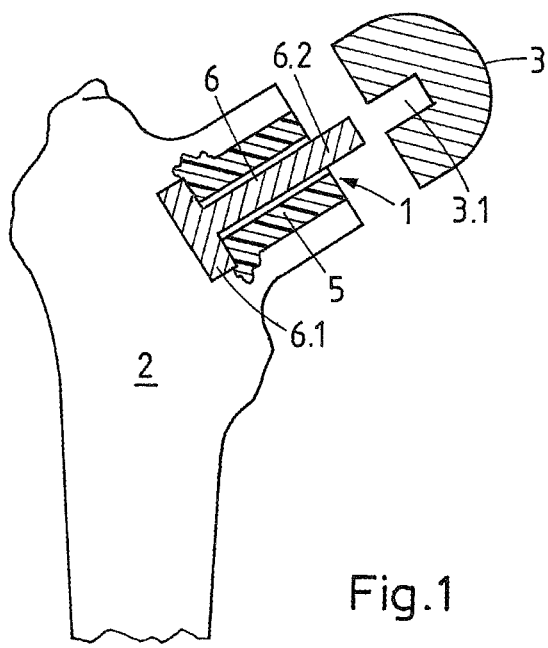
FIGS. 1 and 2 illustrate a first exemplary embodiment of the invention concerning anchorage of an endoprosthesis for resurfacing a femoral head, wherein the counter element is located between the distal and the proximal end of the vibrating element, which reaches through the counter element, wherein the liquefiable thermoplastic material is comprised by the counter element, and wherein the produced implant is constituted by the vibrating element and a part of the counter element.
Figure 2:
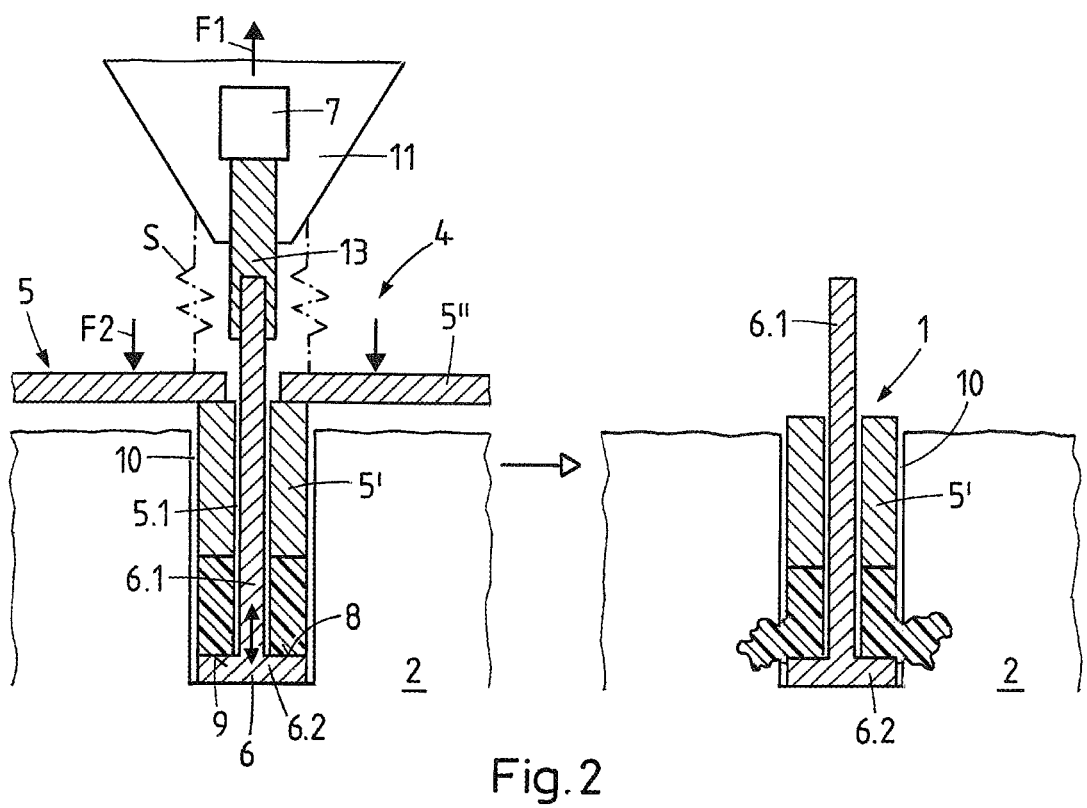

FIGS. 1 and 2 illustrate implantation of a hip joint prosthesis wherein a shaft of the prosthesis is an implant which is anchored in an opening of the correspondingly prepared femoral bone using a first exemplary embodiment of the method and the device according to the invention. FIG. 1 shows the implant 1 which is anchored in the femoral bone 2 and constitutes a prosthesis shaft to which an outer prosthesis part 3 is to be attached. FIG. 2 shows in a larger scale on the left hand side the device 4 according to the invention being positioned relative to the femoral bone 2 ready for the anchoring process, and, on the right hand side, the anchored implant 1 after the anchoring process.

In addition to the femoral application shown in FIG. 1 there are many other applications for the anchoring method as shown in FIGS. 1 and 2. Therein the outer prosthesis part 3 is replacing a bearing surface, which may be convex (e.g. ball of hip joint, femoral side of a knee joint, extremity joints, tempora-mandibular joint), concave (e.g. joint socket of shoulder joint, socket for acetabular reconstruction) or substantially even (e.g. tibia plateau, extremities, spinal facets), or it serves as replacement of the whole joint part (joint ball or joint socket).

The device 4 used for anchoring the prosthesis shaft (implant 1) according to FIG. 1 is designed according to the following principle: the counter element 5 comprising two parts 5' and 5" is positioned between the distal and the proximal end of the vibrating element 6, the vibrating element 6 reaches through the counter element 5, the contact face 8 of the vibrating element 6 faces towards the proximal end of the vibrating element, and the counter element 5 comprises the liquefiable thermoplastic material in the area of its contact face 9. The holding forces F1 and F2 put a tensile load on the vibrating element 6 and a compressive load on the counter element 5.

As clearly seen in FIG. 2, the vibrating element 6 (e.g. sonotrode of an ultrasonic device) comprises a stem 6.1 of a smaller cross section and a distal end piece 6.2 of a larger cross section, the proximal face of the end piece 6.2 constituting the contact face 8. In the illustrated embodiment the vibrating element does not comprise the liquefiable thermoplastic material but is made e.g. of a metal. The contact face 8 extends around the stem 6.1 e.g. in a direction perpendicular thereto.

The counter element 5 comprises a distal part 5' (nearest to the vibrating part and comprising the contact face 9) in the form of a tubular member with a distal portion of the liquefiable thermoplastic material and a proximal portion of a non-liquefiable material, e.g. of a metal, the two portions being connected to each other e.g. by being glued together or by a positive-fit connection. The distal face of the tubular member 5' constitutes the contact face 9. The cross section of the stem 6.1 (circular or non-circular) is adapted to the opening 5.1 in the tubular member such that the latter is able to sit loosely on the stem 6.1. The end piece 6.2 and the tubular member have advantageously the same cross section (circular or non-circular) which is adapted to the cross section of an opening 10 provided in the femoral bone 2. The counter element 5 may further comprise a proximal part 5" (further distanced from the contact face 8 of the vibrating element than part 5') through which the second holding force F2 is applied. The proximal part 5" of the counter element 5 has e.g. the form of a plate comprising an opening 5.1 like the distal part 5', through which opening the stem 6.1 of the vibrating element 6 reaches. The plate 5" consists of a non-liquefiable material, e.g. of a metal (no further liquefaction between the two further contact faces of parts 5' and 5").

The device 4 comprises in addition to the vibrating element 6 and the counter element 5 a vibration source 7 (or hand piece) to which the vibrating element 6 is connected in a per se known manner suitable for transmission of the vibration from the vibration source 7 to the proximal end of the vibrating element 6, and which preferably comprises a non-vibrating housing 11 to which the holding force F1, to act on the vibrating element 6, is applied.

The device 4 is pre-assembled by pushing the stem 6.1 through the counter element 5 (tubular member 5' and, if applicable, plate 5") and by attaching it to the vibration source 7 e.g. by screwing it into an adapter 13 which is rigidly fixed to the vibration source. The device 4 is then positioned relative to the opening 10 provided in the tissue (as illustrated on the left hand side of FIG. 2) such that the end piece 6.2 and the contact face 8 are positioned within the opening 10 and the plate 5" being positioned at least partly outside the opening 10 is able to push the tubular member 5' against the contact face 8. The two holding forces F1 and F2 and the vibration are then applied. The vibrating element 6 and the counter element 5 are held and then moved against each other such liquefying the thermoplastic material of the contact face 9 and then making the liquefied material flow from between the contact faces 8 and 9 and to get into contact with the tissue surface surrounding the outer edges of the two contact faces 8 and 9 and to penetrate into this tissue as shown on the right hand side of FIG. 2. The vibration is then stopped, the holding forces preferably maintained until the liquefied material is re-solidified and then the vibrating element 6 is separated from the adapter 13 and the proximal part 5" of the counter element (if applicable) is removed.

The implant 1 produced according to the method as described above and as shown in FIG. 1 and on the right hand side of FIG. 2 comprises the vibrating element 6 as well as the distal part 5' (tubular member) of the counter element 5, wherein this tubular member 5' is anchored in the femoral bone tissue 2 by the positive-fit connection created by liquefaction, displacement and re-solidification of the thermoplastic material, and wherein the vibrating element 6 is retained in the opening 10 by the anchored part 5' of the counter element 5.

For attachment of the outer prosthesis part 3, the proximal end of the stem 6.1 of the vibrating element 6, which proximal end protrudes from the opening 10 in the femoral bone 2, is adapted to an opening 3.1 in this outer prosthesis part 3 e.g. for a tapered connection. Any other per se known means may serve for attaching the outer prosthesis part 3 to the stem 6.1 of the vibrating element 6.

As shown in FIG. 2, the vibrating element 6 has the same position relative to the femoral bone 2 before and after the anchoring process. This means that the vibrating element 6 and therewith the vibration source 7 or hand piece are kept, during the anchoring process, in the same position relative to the bone by e.g. the housing 11 being fixed relative to the bone. This means that the counter element 5 is moved towards the tissue. Movement relative to the bone tissue of the counter element 5 only, is particularly suitable for the embodiment as illustrated in FIGS. 1 and 2 in which the vibrating element 6 is maintained between the bottom of the opening 10 and the anchored part of the counter element 5, which position is the more stable the better adapted this space is to the end piece 6.2 of the vibrating element 6.

If the thermoplastic material of the counter element 5 has a suitably low melting temperature and if the contact faces 8 and 9 are suitably small, liquefaction occurs easily and with an acceptable energy (and therefore acceptable thermal load on the tissue) even if the two contact faces 8 and 9 are both even and lie fully against each other. Experiments show that this is the case for a thermoplastic material such as e.g. PLLA and contact faces in the region of 10 to 20 mm2. For thermoplastic materials of a higher melting temperature or glass transition temperature respectively and/or for larger contact faces it is advantageous to equip one of the contact faces 8 or 9 with energy directors, i.e. with protrusions in the form of ribs or humps which reduce the first contact between the contact faces to narrow lines or small points. Particularly advantageous are energy directors in the form of radially extending ribs which, between them, form radially extending channels, through which the liquefied material can flow to the outer edges of the contact faces and away from the vibrating element and counter element. The energy directors may be provided on either one of the contact faces 8 or 9, i.e. may either consist of the non-liquefiable material of the end piece 6.2 or of the liquefiable material of the distal portion of the tubular member 5'.

Figure 3:
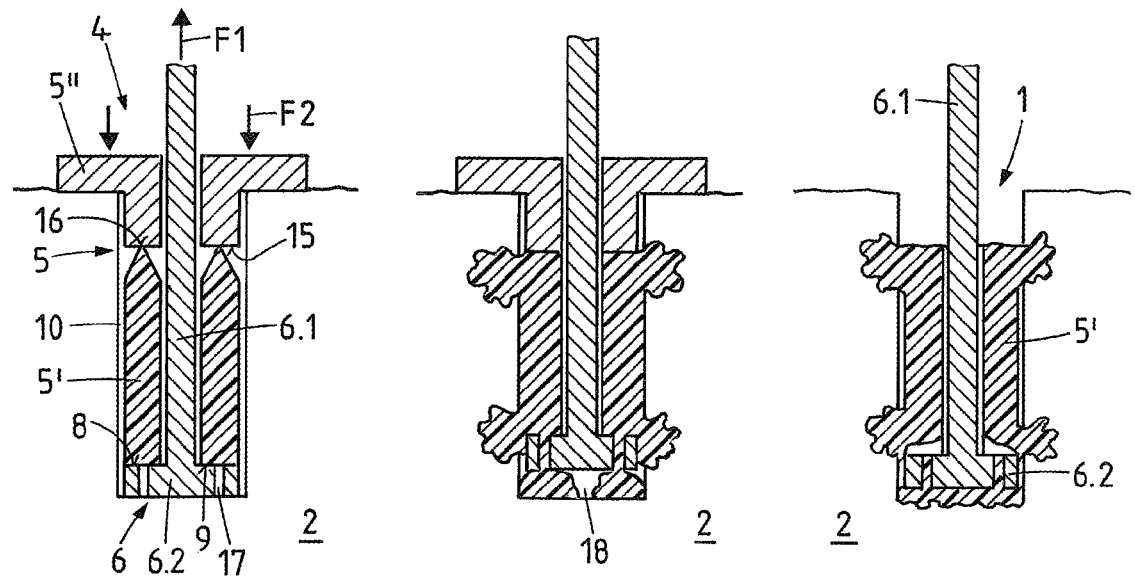
FIGS. 3 and 4 illustrate two further embodiments of the invention which base on the same principle as the first embodiment.
Figure 4:
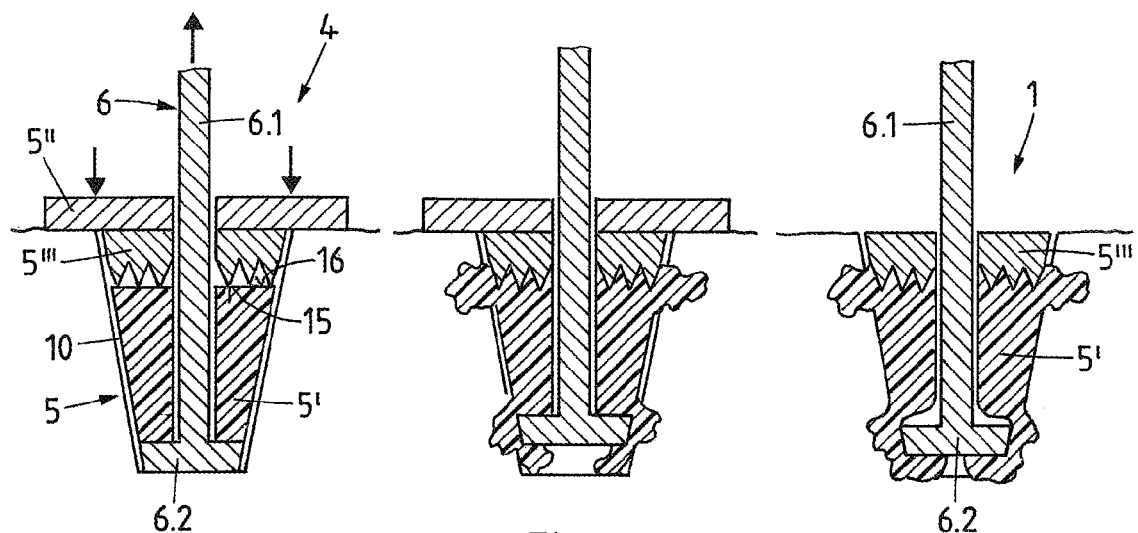

FIGS. 3 and 4 show in the same manner as FIG. 2 further exemplary embodiments of device and method according to the invention which embodiments are based on the same principle as the embodiment as discussed in connection with FIGS. 1 and 2 and therefore are advantageous for substantially the same applications. Same numerals are used for designating same items.

The device 4 according to FIG. 3 is shown on the left hand side of FIG. 3 positioned relative to an opening 10 provided in the tissue ready for the application of the holding forces F1 and F2 and the vibration. The device 4 differs from the device according to FIG. 2 by the distal part 5' of the counter element 5 consisting fully of the liquefiable thermoplastic material, such that liquefaction becomes possible also between the distal part 5' and the proximal part 5" of the counter element 5 (further contact faces 15 and 16), and by the end piece 6.2 of the vibrating element 6 comprising through bores 17 reaching from the contact face 8 to the distal face of the end piece.

Additional liquefaction between the further contact faces 15 and 16 results in anchorage in two locations (as shown in the middle of FIG. 3) as opposed to anchorage in one location only as shown in FIGS. 1 and 2. Such two-point anchorage is relevantly more stable than the one-point anchorages.

If the further contact faces 15 and 16, regarding material and form, are substantially the same as the contact faces 8 and 9, there will be considerably less liquefaction between the further contact faces 15 and 16 than between the contact faces 8 and 9, because due to the poor vibration transmission through the contact faces 8 and 9 there is considerably less vibration energy available at the further contact faces 15 and 16. This effect can be altered by providing, at the proximal end of the tubular member 5', a liquefiable thermoplastic material of a relevantly lower melting temperature or glass transition temperature respectively than the corresponding temperatures of the material of the distal end and/or by giving the further contact faces 15 and 16 relevantly less effective contact area. The effective contact area is reduced by e.g. designing the proximal end (further contact face 16) of the tubular member tapering and the distal end (contact face 9)

flat or by providing energy directors between the further contact faces 15 and 16, but not between the contact faces 8 and 9.

The proximal part 5" of the counter element 5 can be removed after the anchorage process (as shown on the right hand side of FIG. 3) if it consists of a non-liquefiable material and the liquefied material of the distal part 5' does not adhere thereto.

The bores 17 provided in the end piece 6.2 will allow that at least a part of the material being liquefied between the contact faces 8 and 9 can flow to the distal side of the end piece 6.2. When providing such through bores 17, it may be advantageous to move the vibrating element 6 relative to the opening during the anchoring process and to keep the counter element 5 stationary relative to the bone tissue, thus creating a space 18 between the end piece 6.2 and the bottom of the opening 10, into which space 18 some of the liquefied material will flow through the bores 17, as shown in the middle of FIG. 3. This material can be impacted and made to penetrate the named bottom if in a further method step the vibrating element 6 is pushed against this bottom when enough material is liquefied and at least part of it is still liquid, i.e. able to penetrate the tissue on the bottom of opening 10.

Of course the impactation step may be omitted, in particular if the tissue at the bottom of the opening 10 is easily penetrated or does not need to be penetrated. It is possible also to adapt the feature of the bores 17 through the end piece 6.2 in the method as illustrated in FIG. 2, wherein the above mentioned impactation is not possible (unless the opening goes deeper than the initial position of the end piece 6.2), but liquefied material can still flow through the bores and penetrate the bottom of the opening.

The implant 1 produced in the method as illustrated by FIG. 3 consists of the tubular member (distal part 5' of counter element 5), which is anchored in the region of its distal end and its proximal end, and of the vibrating element 6 whose end piece 6.2 is embedded in the liquefiable thermoplastic material.

FIG. 4 shows a further exemplary embodiment of device and method according to the invention, which embodiment is based on the same principle as the embodiment discussed in connection with FIGS. 1 to 3 and it is therefore advantageous for similar applications as listed in connection with FIGS. 1 and 2. Same items are designated with same reference numerals.

Other than shown in FIGS. 2 and 3, according to FIG. 4, the opening 10 provided in the tissue is not substantially cylindrical but it is conical, i.e. is wider at its moth than at its bottom. Furthermore the counter element 5 comprises three parts: the most distal part 5' (nearest the contact face of the vibrating element) comprising the contact face 9 and consisting of the liquefiable thermoplastic material, the most proximal part 5" (most distanced from the contact face of the vibrating element) to which the second holding force is applied and which consists of a non-liquefiable material, and the middle part 5''' consisting of a non-liquefiable material also.

The size of the end piece 6.2 is adapted to the bottom of the opening 10 and the vibrating element 6 is moved away from this bottom during the anchoring process and thereby opens a lateral passage for the liquefied material to flow between the bottom of the opening 10 and the end piece 6.2 of the vibrating element. At the end of the anchoring process the vibrating element is advantageously pushed against the bottom of the opening 10 and therewith closes the named passage which will render the impactation of the liquefied material between the end piece 6.2 and the bottom of the opening more effective.

The same as described in connection with FIG. 3, also according to FIG. 4 there are further contact faces 15 and 16 between the most distal part 5' and the middle part 5''' of the counter element 5. One of these contact faces 15 or 16 is equipped with energy directors which advantageously have an undercut form such that on re-solidification of the thermoplastic material, which will be liquefied and remain between these contact faces, a positive fit connection will form between the parts 5' and 5'''.

The implant 1 produced in the method as illustrated in FIG. 4 is constituted by the vibrating element 6 and by the parts 5' and 5''' of the counter element 5 (part 5" is removed), wherein the part 5' is anchored on its distal side in the tissue of wall and bottom of the opening 10 and on its proximal side in the tissue of the wall of the opening 10 and wherein the end piece 6.2 of the vibrating element is embedded in the thermoplastic material.

Further variants of the embodiment of method and device according to the invention as illustrated by FIGS. 1 to 4 result from the following alterations:

- By providing a suitably shaped end piece 6.2 (e.g. bar) and an adapted opening 5.1 (e.g. slot adapted to the bar) in the counter element 5, the vibrating element 6 becomes removable from the counter element 5. For such removal, the vibrating element is rotated from an active rotation position, in which it is in contact with the contact face of the counter element 5, into a removal position, in which it is aligned with the opening 5.1. In such a case, the implant 1 is constituted by the counter element 5 or part thereof alone and the outer prosthesis part 3 may e.g. comprise its own shaft adapted to the proximal end of the opening 5.1 of the counter element 5 or part thereof to allow fixation therein.
- The opening 10 in the tissue in which anchorage is to be achieved is a through opening (tunnel) and the vibrating element 6, when detached from the vibration source 7, is removed from the tunnel in a direction away from the vibration source 7.
- The counter element 5 or its most proximal part 5" respectively is connected to the housing 11 of the vibration source via a pre-tensioned (compressed) spring (shown in FIG. 2 in dash-dot lines designated with S), which pushes the counter element 5 away from the housing 11 and against the end piece 6.2 such exerting both holding forces F1 and F2 and causing the movement of the two elements 5 and 6 against each other as soon as liquefaction of the thermoplastic material starts. A surgeon handling the device can in this case move this device freely relative to the tissue in which anchorage is to be achieved, i.e., if a sufficiently deep opening is provided in the tissue he can freely select the depth in which he wants to achieve the anchorage. Generally speaking, the vibrating element 6 and the counter element 5 are arranged to be members of a load frame comprising in any suitable location a biasing element, which is e.g. a spring, a pneumatic or hydraulic cylinder or a screw jack.
- The vibrating element 6 comprises the liquefiable thermoplastic material in the area of its contact face 8 while the distal end of the counter element 5 does not comprise any liquefiable material. Therefore, it is the vibrating element 6 which is anchored in the opening 10 while the counter element 5 may be removed from the opening 10 after the anchoring process.

Both contact faces 8 and 9 comprise a liquefiable thermoplastic material, the two thermoplastic materials being weldable to each other with the aid of the vibration such that both the vibrating and the counter element remain joined together after the anchoring process, both constituting a part of the implant 1 and both being anchored in the tissue. The same is possible for further contact faces between parts of the counter element.

One of the contact faces 8 and 9 comprises the liquefiable thermoplastic material and the other one comprises a surface structure (e.g. porosity, undercut cavities or protrusions) which is penetrated by the liquefied material and, on re-solidification forms a positive fit connection therewith. Such surface structure may also serve as a plurality of energy directors in the liquefaction process. The same may be provided at further contact faces.

The counter element 5 may comprise one part only.

The contact faces 8 and 9 are not even and/or extend at an oblique angle relative to the axes of the vibrating element 6 and the counter element 5.

The stem 6.1 of the vibrating element 6 is replaced by a cable or other flexible member which is able to transmit the vibration to the end piece 6.2 and to withstand the tensile load applied to it by the two opposite holding forces F1 and F2. Such cable or other flexible member allows a non-linear axis of the counter element.

Anchorage as illustrated in FIGS. 1 to 4 is effected in a jaw bone, the implant 1 constituting a dental implant to which an abutment or other supra-structure is mounted in a similar way as described for the outer prosthesis part 3.

FIG. 5 illustrates a further embodiment of the device and method according to the invention which is used for anchoring a dental implant 20 (implant 1) in a jaw bone 21 and which again is based on the same principle as the embodiments according to FIGS. 1 to 4. The anchoring process is shown in five successive phases A, B, C, D and E.

Other than shown in FIGS. 1 to 4, the end piece 6.2 of the vibrating element 6 comprises a liquefiable thermoplastic material, which may be the same as the thermoplastic material of the counter element 5 or a different thermoplastic material which is preferably weldable to the thermoplastic material of the counter element 5. Furthermore, the counter element comprises a proximal flange 5.2 which at least on its distal face comprises the liquefiable thermoplastic material and the vibrating element 6 comprises a proximal portion having a larger cross section than the stem 6.1, wherein a shoulder 6.3 is provided between the proximal portion and the stem 6.1, the shoulder being adapted to the proximal flange 5.2 of the counter element.

The stem 6.1 of the vibrating element is made of a non-liquefiable material e.g. of a metal and comprises on its distal end a thread or other surface structure suitable for being connected to the walls of a corresponding depression e.g. bore in the end piece 6.2, wherein the end piece e.g. consists fully of the liquefiable thermoplastic material or comprises the latter at least in the area of the depression.

The device 4, which again comprises the vibrating element 6 being attached to a vibration source (not shown) and the counter element 5 is pre-assembled by e.g. fixing the stem 6.1 of the vibrating element 6 to the vibration source, positioning the counter element 5 on the stem 6.1 and then attaching the distal end of the stem 6.1 to the end piece 6.2 by e.g. vibrating the stem and pushing it into the depression or bore of the end piece 6.2 thus liquefying the thermoplastic material in the area of the depression and letting it flow into the thread or other surface structure of the distal stem end. Depending on the cross section of the stem it may be possible also to fix the end piece to the stem in the named manner, without the end piece comprising a corresponding depression or bore.

Phase A shows the pre-assembled device 4 positioned relative to a stepped osseous cavity 22 in the jaw bone 21 in which cavity anchorage is to be achieved. The wider mouth region of the stepped cavity 22 is adapted to the flange 5.2 of the counter element 5. The device 4 is positioned such that the end piece 6.2 and in particular its proximal contact face 8 is positioned within the narrower bottom region of the cavity 22. Therein the counter element 5 and the end piece 6.2 are adapted to each other and to the cavity such that the counter element 5 is able to sit loosely between the end piece 6.2 and the shoulder 6.3 of the vibrating element 6 and that the flange 5.2 of the counter element 5 is able to sit on the step of the cavity 22 when the end piece 6.2 and the distal portion of the counter element are positioned within the cavity.

As shown with the aid of corresponding arrows, the vibrating element 6 is then vibrated and pressed against the jaw bone 22 with the effect of the distal face of the flange 5.2 being pressed against the step in the cavity 22 and being anchored (see phase B) in a per se known manner therein. For enhancing liquefaction of the distal face of the flange 5.2 this face may comprise energy directors. On the other hand, for preventing liquefaction between the shoulder 6.3 of the vibrating element 6 and the proximal face of the flange 5.2 of the counter element 5, no energy directors are provided at the corresponding contact faces and care is taken that the contact faces are as large as possible and are able to lie exactly against each other.

In phase B, anchorage according to the invention is carried out by again vibrating the vibrating element 6 and pulling it away from the jaw bone (first holding force F1) wherein the flange 5.2 anchored in the step of the cavity 22 counteracts this holding force. Through the vibration the thermoplastic materials of the counter element 5 and of the end piece 6.2 are liquefied in the region of contact faces 8 and 9, and, through the movement of the end piece 6.2 towards the opening of the cavity 22, the liquefied material flows from between the two contact faces 8 and 9 to penetrate the cancellous bone tissue of the cavity wall (see phase C).

In phase C, the vibration is maintained until the liquefiable thermoplastic material of the end piece 6.2 is so soft that the distal stem end can be pulled out of the depression or bore of the end piece 6.2. This pulling-out is effected by increasing the holding force F.1 such that a corresponding movement of the stem 6.1 cannot be compensated by displacement of liquefied material i.e. such that the end piece 6.2 cannot follow and is therefore separated from the stem 6.1, which is then removed (see phase D).

The anchored dental implant 20 (implant 1) as produced in phases A to C and as shown in phase D is constituted by the counter element 5 and the end piece 6.2 of the vibrating element 6 which are connected to each other in the region of the two contact faces and are anchored not only in the wall of the cavity 22 but also in the cavity step. Depending on the capability to be liquefied (in particular on the melting temperature), it is either the counter element or the vibrating element or both elements which are anchored in the cavity wall. The dental implant 20 is again anchored in two locations which renders it particularly stable against lateral and bending loads.

If anchorage in further wall locations is desired, this can be achieved by providing a two- or three-part counter element with further contact faces which are equipped as detailed in connection with FIGS. 3 and 4.

In phase E an abutment 23 or other supra-structure such as e.g. a crown, denture or bridge is attached on the dental implant 20. For such attachment, a shaft of the abutment 23 is e.g. cemented into the opening 5.1 of the counter element 5 or this opening 5.1 comprises an inner thread corresponding to an outer thread of the shaft of the abutment 23. In the latter case it may be advantageous if the proximal portion of the opening 5.1 comprises a non-liquefiable material such as e.g. a metal or a ceramic material.

Obviously, the method as illustrated in FIG. 5 can be carried out without loading inner regions of the cancellous bone of the jaw bone. The only load on the jaw bone occurs in phase A (anchorage of the proximal portion of the counter element 5 in the step of the cavity 22) and concerns outer regions of the jaw bone, i.e. corticalis and/or denser outer cancellous bone, being better suited for carrying a load. It is the same bone region which counteracts the holding force F1 in the process in which the dental implant is anchored in the cavity walls. If such loading of the bone tissue is not desired, a counter element without flange 5.2 can be used and the holding forces can be applied to the vibrating element 6 and the counter element 5 by biasing the vibrating element 6 and the counter element 5 against each other in a load frame, which comprises e.g. a spring similar to the one shown in FIG. 2.

The device 4 and the anchoring process illustrated by phases A to D of FIG. 5 are adaptable to many other applications wherein the preliminary step of anchoring a proximal section of the counter element in a step of an opening or bore provided in the tissue or around the mouth of a tissue opening may be applicable or not. One example of such application is the one illustrated in FIG. 1, wherein other than shown in FIG. 1, the implant does not include the stem of the vibrating element and therefore, the outer prosthesis part needs to be provided with a suitable shaft, and wherein the counter element is advantageously equipped with a proximal flange which is anchored in the face of the suitably prepared bone.

Principally, it is possible to use implants 1 as shown in FIG. 5 in most known applications in which according to the state of the art screwed implants are used. Examples of further applications are shown in FIGS. 6 and 7.

FIG. 6 shows an endoprosthesis 25 for resurfacing a joint socket, e.g. for the fixation of the acetabular cup of a hip joint reconstruction. The endoprosthesis is fixed to the correspondingly prepared bone tissue by a plurality of implants which are similar to the implant 1 as shown in FIG. 5 (phase D) and are produced with the same method as illustrated in FIG. 5. Therein the counter elements 5 are not supported by a step in an opening provided in the tissue or by the bone surface surrounding the opening in which anchorage is to be achieved (which in the present case is not mechanically stable corticalis or dense enough cancellous bone) but by the whole cup-shaped endoprosthesis, and is therefore supported by a much larger area. Proximal flanges 5.2 of the counter elements 5 may also be anchored in the endoprosthesis which for this purpose comprises a corresponding depression and surface structure around openings provided for the implants.

The advantage of the method according to FIG. 5 in the application of FIG. 6 is the ease, in which a plurality of anchorages can be produced. For this purpose it is advantageous to provide pairs of end pieces 6.2 and tubular counter elements 5 in a container each, in which container the end piece 5.2 is positioned on the bottom and the counter element 5 is maintained on the end piece and aligned therewith. When one anchorage is produced, the stem 6.1 of the vibrating element which remains attached to the vibration source is equipped with a further pair of a counter element 5 and an end piece 6.2 by using one of the containers charged with an end piece 6.2 and a counter element 5. The distal stem end is simply pushed through the opening of the counter element and into the depression of the end piece, while the stem is briefly vibrated for fixing the end piece to its distal end. When the stem is removed from the container, the counter element 5 and the end piece 6 are attached to it and the device is therefore ready for the next anchoring process.

Obviously, the same procedure as illustrated by FIG. 6 is possible also for fixing a convex or substantially even resurfacing prosthesis to a correspondingly prepared bone surface or for fixing a supporting plate to a bone surface, e.g. for stabilizing a bone fracture in an osteosynthesis process. In the same manner, a soft tissue such as a tendon or ligament can be attached to a bone surface.

FIG. 7 shows a marrow space sealing, e.g. to be used as cement stopper for the cementation of the stem of a hip endoprosthesis. The cement stopper is produced with the method as illustrated in FIG. 5 (without the preliminary step of anchoring a proximal flange the counter element). The sealing element (implant) produced is constituted by the end piece 6.2 of the vibrating element 6 and a distal part 5' of the counter element 5. The proximal part 5" of the counter element 5 is used only for holding the counter element part 5' against the contact face 8 of the vibrating element 6 and is removed after the anchoring process. The contact faces 8 and 9 and the further contact faces 15 and 16 are advantageously designed such that there is liquefaction also between the further contact faces 15 and 16 but no joining of the parts 5' and 5" of the counter element 5.

In a similar manner, a sealing element can be produced in a bone cavity produced by removing tissue (e.g. cavity produced by removing a dental root) or for limiting a bone cavity against a sensitive tissue (e.g. for protecting the anterior wall of a vertebra to allow a safer cement injection during vertebroblastic restoration of the vertebral height).

FIG. 8 illustrates the application of an embodiment of device and method according to the invention and based on the same principle as the embodiments according to FIGS. 1 to 7 for repairing soft tissue, e.g. a laceration 27 in meniscal tissue 28. The device 4 which again comprises a vibrating element 6 reaching through a two part counter element 5 and a vibration source (not shown) is positioned relative to the tissue 29 by inserting its distal end into the tissue 28 through a small incision 29 and advancing it inside the tissue across the laceration 27.

When the end piece 6.2 of the vibrating element and a distal portion of the counter element part 5' are positioned beyond the laceration and the further contact faces between the parts 5' and 5" are positioned on the proximal side of the laceration but inside the tissue, the holding forces and the vibration are applied to liquefy the thermoplastic material of the counter element and possibly the end piece and letting it flow into the tissue. After re-solidification of the liquefied material the stem 6.1 of the vibrating element and the proximal part 5" of the counter element 5 are removed from the tissue.

The meniscal tissue 28 which in its natural state does not comprise cavities or pores is locally displaced by the liquefied material, i.e. cavities are produced by the liquefied material, and the tissue closes itself around the implant also closing the initial incision thus completely embedding the implant 1. Preferably the implant which is constituted by the distal part 5' of the counter element 5 and the end piece 6.2 of the vibrating element 6 consists of a resorbable material such that, on healing of the laceration 27, it disappears.

FIGS. 9 to 11 show further embodiments of the method and device according to the invention, which embodiments again are based on the same principle as the embodiments according to FIGS. 1 to 7 and are applicable in particular for securing two tissue parts, in particular two bone parts, wherein the produced implant 1 reaches through the first tissue part into the second tissue part and assumes the function of a tension screw. The method corresponds, as far as the anchoring process according to the invention is concerned, with the embodiment according to FIG. 5 and may also include the preliminary step of anchoring a proximal flange of the counter element in a step of the opening provided in the first tissue part or to an outer surface thereof. Other than the method according to FIG. 5, the present method comprises an additional preliminary step, in which the end piece 6.2 of the vibrating element 6 is secured in the second tissue part.

The opening provided in the tissue parts and the implant 1 extend from the surface of the first tissue part through the first tissue part into the second tissue part, wherein the counter element 5 comprises a proximal flange for retaining the proximal end of the counter element in the mouth region of the opening and the end piece of the vibrating element is preliminarily secured in the second tissue part before it is joined to the counter element. The two holding forces do therewith not only hold the vibrating and the counter element against each other but also the two tissue parts and the movement of the vibrating and the counter element against each other is stopped, when the two tissue parts are placed against each other. By increasing the holding force to a force of a size as applied to a known tension screw, the two tissue parts can be biased against each other and on releasing the holding forces after re-solidification of the thermoplastic material the implant is under a tension load in the same way as a known tension screw.

FIG. 9 shows the above described method for securing two fragments 32.1 and 32.2 of a fractured tubular bone 32 with a marrow nail 30 (implant 1), which is anchored in the walls of the marrow space 31 of the tubular bone 32.

The tubular counter element 5 again comprises a proximal flange 5.2 which may or may not be anchored in the corresponding step of the opening through the bone wall of the first bone fragment 32.1. Whether anchored or not, the flange 5.2 serves as proximal fixation of the counter element 5. The vibrating element 6 again comprises a stem 6.1 and an end piece 6.2 of a liquefiable thermoplastic material which end piece 6.2 is initially fixed to the distal end of the stem 6.1, which connection is separated at the end of the anchoring process according to the invention.

In a preliminary method step the end piece 6.2 is secured in the second bone fragment in a per se known manner, preferably by making the end piece 6.2 completely of the liquefiable thermoplastic material and by vibrating it and simultaneously pressing it into the opening in the second bone fragment which, for this preliminary anchorage, comprises a blind bottom or a tapering bottom region. In this preliminary method step, the counter element 5 and the vibrating element 6 have aligned axes but they are not held against each other. During this preliminary method step, the distance between the contact faces 8 and 9 should remain smaller than the distance between the two bone fragments.

Of course it is possible also to secure the end piece 6.2 in the second bone fragment 32.2 with other securing methods such as e.g. by providing the end piece 6.2 with a self-tapping thread and by screwing it into the marrow space wall of the second bone fragment 32.2.

As soon as the end piece 6.2 is secured in the second bone fragment 32.2, the main anchoring step is carried out as described in detail in connection with FIG. 5, wherein through the movement of the end piece 6.2 against the counter part 5, which, due to the flange 5.2 being anchored in the first bone fragment or being held against this by a second holding force, remains stationary relative to the first bone fragment 32.1, the second bone fragment 32.2 is pulled against the first bone fragment 32.1 until the two bone fragments are biased against each other such that no further movement can be achieved by the action of the holding forces. The vibration is then stopped to let the thermoplastic material to re-solidify to form a stable connection between the counter element 5 and the end piece 6.2. The holding forces are then released. There is a tensional load on the resulting implant 1 between its flange 5.2 sitting on the outer surface of the first bone fragment 32.1 and its distal end being secured in the second bone fragment 32.2, which tension biases the two bone fragments against each other. The right hand side of FIG. 9 shows the marrow nail 30 (implant 1) after the anchoring process and after removal of the stem 6.1 of the vibrating element 5.

In the method as illustrated in FIG. 9, the stem 6.1 of the vibrating element 6 has two functions. In the preliminary step of anchoring the end piece 6.2 in the bone surface of the marrow space, the stem needs to be able to press the end piece 6.2 against this bone surface (compressive load on the stem). In the following step in which liquefaction between the end piece 6.2 and the counter element 5 is to be achieved, the stem 6.1 needs to be able to pull the end piece 6.2 together with the second bone fragment 32.2 against the first bone fragment 32.1 (tensile load on the stem). If there is substantially no angle between the proximal and the distal portion of the counter element 5 the stem 6.2 is preferably a stiff element as for the above described embodiments. If there is such an angle, as shown in FIG. 9, it may be necessary to use a different stem for the preliminary step and even to introduce this stem differently then shown for the stem 6.1, such that it is able to apply a pressing force to the end piece as required for its anchorage. The stem 6.1 used for the anchoring process according to the invention can then be realized as a flexible cable and therefore accommodate the named angle without a problem.

FIG. 10 illustrates very schematically stabilization of a fractured femoral neck which is achieved in substantially the same manner as above detailed for securing a fractured tubular bone. Therein the proximal end of the counter element 5 is supported by a marrow nail which may be secured in the marrow space as detailed in connection with FIG. 9 or it may be anchored in the marrow space of the femoral bone by any other known method. FIG. 10 shows the implant 1 which secures the fractured femoral neck just before removal of the stem 6.1 of the vibrating element.

Instead of supporting the proximal end of the counter element 5 in a marrow nail 30 as shown on FIG. 10, it is possible also to support the counter element in a trochanter plate positioned on the outer surface of the femoral bone or on this outer surface of the femoral bone directly.

Further applications for the device and the method as illustrated in FIGS. 9 and 10 are all sorts of fracture reduction and fracture fixation applications in which, according to the state of the art, lag-screws or cannulated screws are used. Therein the implants produced with the method according to the invention may constitute stand-alone devices or may cooperate with plates, nails or external fixators. It is possible also that at least some of the bone fragments to be re-joined are not native bone tissue but are grafted bone tissue or bone replacement material. Such further applications are e.g. pedicle screws in spinal surgery, reduction of clavicular fractions, repair of fractured distal radius, ulna or patella or closure of osseotomies such as e.g. created in the sternum for heart operations.

FIG. 11 illustrates, again very schematically, fusion of a facet joint with an implant similar to the one used for securing the fractured femoral neck according to FIG. 10. Similar fusion processes are applicable for small joints of hand or foot.

A further application of the method and device as illustrated in FIGS. 9 to 11 is e.g. fixation of a ligament, tendon or other soft tissue relative to a bone surface, wherein thanks to the tensile loading, which is able to be built up in the implant, the ligament, tendon or other soft tissue is held securely against the bone surface.

Figure 12:
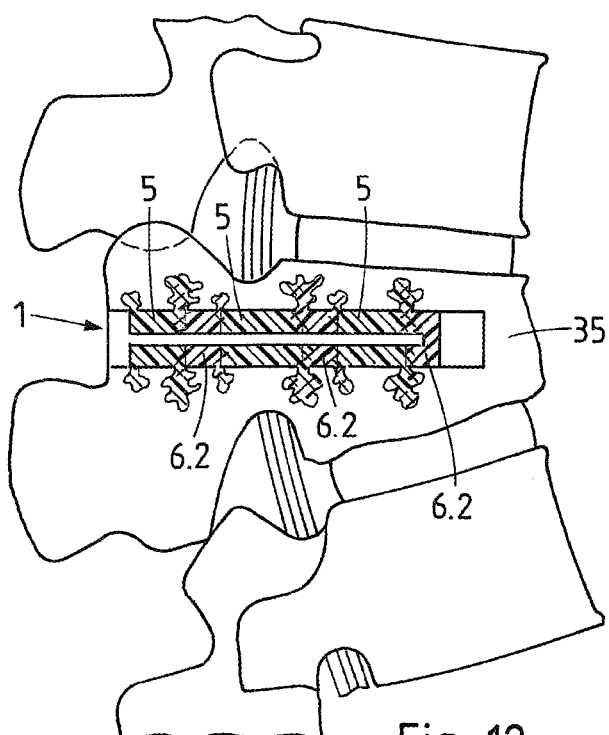
FIGS. 12 and 13 illustrate a multi-step method according to the invention applied for reconstruction of a collapsed vertebral body, wherein each step of the method corresponds with the method illustrated by FIG. 5.
Figure 13:
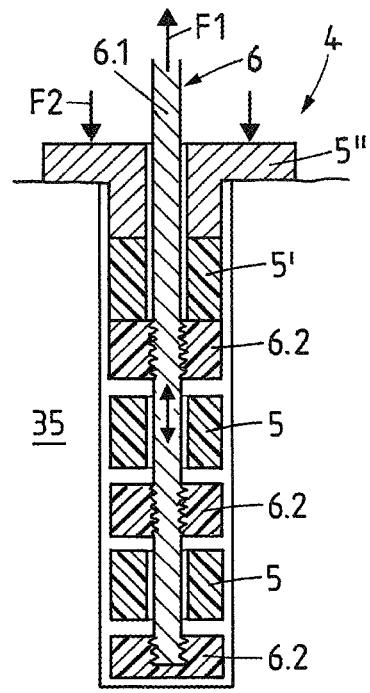

FIGS. 12 and 13 illustrate reconstruction of a collapsed vertebral body 35 with the aid of a further exemplary embodiment of the invention. Obviously, the implant 1 produced in this application is anchored in the vertebral body 35, however, its main function consists in strengthening the remaining tissue of the collapsed vertebral body 35 and augmenting its height through the implant 1 and in particular through the thermoplastic material which in a liquid state flows from between the elements of the device into the tissue. The method illustrated in FIGS. 12 and 13 corresponds in principle to the method as shown in FIG. 5 (without preliminary anchoring of the counter element in the region of an outer surface of the vertebral body) but allows a plurality of anchoring steps according to the invention. FIG. 12 shows the implant 1 after the multi-step anchoring procedure and FIG. 13 shows a corresponding device 4 in a larger scale and positioned relative to the vertebral body 35 for the anchoring process. The device 4 is introduced into an opening in the collapsed vertebral body 35, wherein such opening may be provided in the vertebral body or wherein only a preliminary opening is provided and the distal end of the device is then pushed further into the vertebral body.

The device 4 comprises a vibrating element 6 with a stem 6.1 to which a plurality of end pieces 6.2 is fixed, wherein the end pieces 6.2 are distanced from each other and between end pieces tubular counter elements 5 sit loosely on the stem 6.1 and wherein both the end pieces 6.2 and the counter elements 5 substantially consist of the liquefiable thermoplastic material. The most proximal counter element comprises two parts 5' and 5" which are designed as e.g. detailed in connection with FIG. 2 (no further liquefaction between parts 5' and 5"). FIGS. 12 and 13 show three end pieces and three counter elements. However, there could be more or less than three end pieces and counter elements which would not change the principle of the method.

The pre-assembled device 4 (see FIG. 13) is adapted to the opening in the vertebral body 35 such that, when the most distal end piece is positioned against the bottom of the opening, the most proximal end piece is positioned within the opening. The device is such positioned and is held in the opening by applying the second holding force to the proximal part 5" of the most proximal counter element, wherein this part 5" is supported by the outer surface of the vertebral body 35 or by any other suitable support which has a stationary position relative to the vertebral body. On application of the first holding force F1, the most proximal end piece 6.2 is held and then moved against the most proximal counter element 5. When liquefaction or at least plastification of the thermoplastic material of the end piece reaches the region of the end piece, in which the stem 6.1 is fixed and the first holding force is momentarily increased the stem 6.1 moves relative to the most proximal end piece and therewith the next end piece is held against the next counter element and the anchoring process is repeated, wherein the second counter element may also be welded to the most proximal end piece and liquefied material may there also flow from between the contact faces but not predominantly (see FIG. 12). The same applies for all further end pieces 6.2 and counter elements 5 until eventually the most distal end piece is separated from the stem 6.1 and the stem can be removed.

In all FIGS. 1 to 13 it is assumed that the vibrating element comprises one stem 6.1 and that this one stem extends through a central opening 5.1 of a tubular counter element 5, wherein the cross section of the tubular counter element 5 and/or of the opening 5.1 is circular or non-circular. The stem serves in the first place for connecting the distal end of the vibrating element 6 with the vibration source which is positioned further proximal than the counter element 5, and in the second place also serves for keeping the counter element aligned with the vibrating element. This one stem 6.1 and one central opening 5.1 is of course no condition for the method according to the invention.

Figure 14:
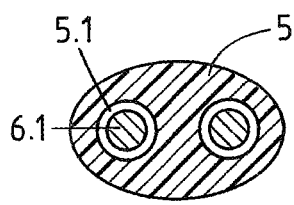
FIGS. 14 to 16 show exemplary cross sections through further examples of vibrating elements reaching through or past a counter element.
Figure 15:
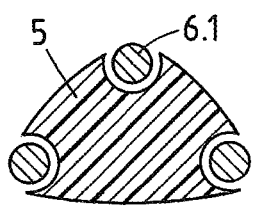
Figure 16:
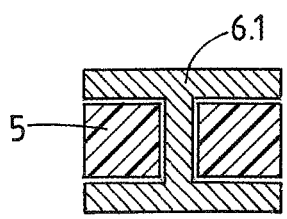

The vibrating element may also comprise one or a plurality of stems 6.1 which extend through the counter element 5 non-centrally as shown in cross section in FIG. 14. Furthermore, a plurality of stems may extend past the counter element 5 which in this case is not tubular at all but may comprise axial grooves adapted to the stems as shown in cross section in FIG. 15. The embodiments of vibrating element and counter element as illustrated in FIGS. 14 and 15 may comprise one end piece only or one end piece per stem. Furthermore, the stem 6.1 may comprise axial grooves in which a plurality of counter elements is positioned. Such an embodiment is shown in cross section in FIG. 16, in which the stem is s double-T-beam and therewith is very resistant against bending and in which the non-tubular counter elements are positioned between the two Ts of the stem, where they are held e.g. by a slight undercut (not shown), into which they are snapped.

FIGS. 17 to 22 illustrate further exemplary embodiments of the method and the device according to the invention, wherein for these embodiments the contact face of the vibrating element is facing away from the proximal end of the vibrating element and the counter element is positioned beyond the distal end of the vibrating element. For enabling application of the two holding forces from the proximal side of the device, the counter element comprises parts (force transmitting member) which reach through or past at least a distal end portion of the vibrating element in the direction towards the proximal end of the vibrating element. The liquefiable thermoplastic material is preferably arranged at the contact face of the counter element and the vibrating element is e.g. made of a metal and has the form of e.g. an ultrasonic horn which is connected directly or indirectly to the vibration source. The implant is in this specific case constituted by the counter element only.

Figure 17:
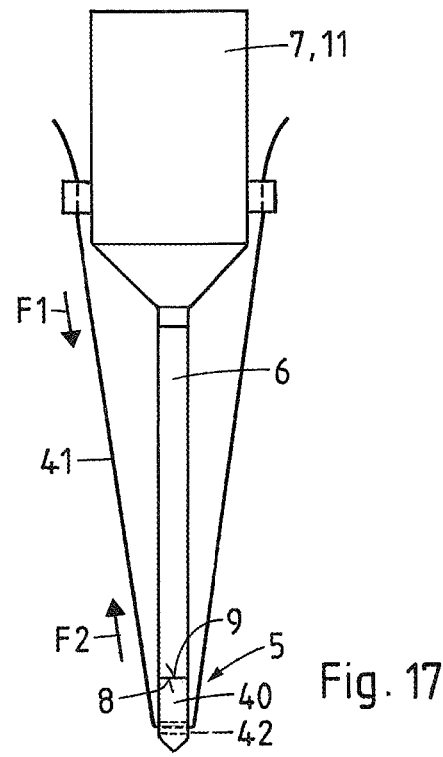

FIGS. 17 and 18 show a suture anchor to be anchored in tissue with the aid of the above mentioned embodiment of the method according to the invention, wherein an anchor body 40 comprising the liquefiable thermoplastic material and the suture 41 (or other force transmitting member) constitute the counter element 5. FIG. 17 shows the whole device for carrying out the method, which device comprises the counter element 5 (anchor body 40 and suture 41) and the vibrating element 6 which is connected to a vibration source 7 located in a non-vibrating housing 11. FIG. 18 shows a preferred embodiment of the anchor body 40 in an axial section and cross sections as well as a top view of the contact face 9 of the anchor body 40.

As seen from FIG. 17 a middle portion of the suture 41 is slideably or non-slideably held in the anchor body 40 by e.g. extending through an opening 42 in a distal region of the anchor body 40. The suture ends are attached to the housing 11 to form a closed load frame. The suture 41 being elastic in a longitudinal direction is tensioned and therewith able to apply both holding forces F1 and F2, i.e. to hold the vibrating element 6 and the counter element 5 against each other and on liquefaction of the thermoplastic material comprised by the counter element 5 in the region of its contact face 9 to move the two elements against each other.

Instead of a suture, another resilient force transmitting member such as e.g. a ribbon can be used. If, instead of a resilient suture or ribbon, a substantially non-elastic wire or cable is to be anchored with the aid of the anchor body as illustrated in FIG. 17 it will be necessary to equip the housing 11 with resilient means for attaching the wire or cable for being able to bias the vibrating element and the counter element against each other and allowing their movement while maintaining the bias.

For anchoring the suture 41 with the aid of the device according to FIG. 17, an opening is provided in the tissue and the anchor body 40 is introduced into the opening to a depth such that the contact face 9 of the anchor body being held against the contact face 8 of the vibrating element 6 is situated within the opening and the outer edges of the contact faces are surrounded by the tissue. The vibration is then started and the liquefiable thermoplastic material being provided in the region of the contact face 9 is liquefied and through the movement of the vibrating element 6 and the counter element 5 against each other is made to flow from between the contact faces 8 and 9 and to penetrate the tissue surrounding the outer edges of these contact faces. Therein the suture 41 will, if no measures against it are provided, be fixed relative to the tissue also.

FIG. 18 shows a preferred embodiment of the anchor body 40 and the distal end of the vibrating element 6 of the device according to FIG. 17, on the left hand side in an axial section and on the right hand side in three cross sections and a top view of the contact face 9. The anchor body 40 has a substantially cylindrical form with a tapering distal end and comprises a proximal portion and a distal portion, wherein the proximal portion carries the contact face 9 and consists of the thermoplastic material which is to be liquefied (e.g. degradable polymer as PLLA or PLDLA 70/30 or PLGA 85/15) and wherein the distal portion is equipped for attachment of the suture, for which attachment, it comprises e.g. a through bore 42 through which the suture extends. For preventing unwanted liquefaction between the suture and the distal portion of the anchor body (further contact faces), the suture as well as the distal portion of the anchor body do not comprise a liquefiable material. The suture is e.g. made of PET or drawn PE (e.g. Dyneema™). The distal portion is e.g. made of PEEK which, although a thermoplastic material, is, when paired with PLLA non-liquefiable. It is of course possible also to make the distal portion of the anchor body 40 of a metal such as e.g. titanium, or of a ceramic material such as e.g. alumina, zirconia or calcium phosphate. If the suture is fixed rigidly to the anchor body, e.g. by being molded into it, there will be no liquefaction at the connection between suture and anchor body even if the distal portion of the anchor body is made of the same material as the proximal portion. The proximal and the distal portion of the anchor body 40 are connected rigidly with each other e.g. by being glued, press-fitted or screwed together.

The contact face 9 of the anchor body 40 (or the contact face 8 of the vibrating element 6) is preferably equipped with energy directors which as shown in FIG. 18 (bottom right) preferably have the form of protruding ribs 9.1 which protrude from the contact face forming radial channels between themselves which channels facilitate radial flow of the liquefied material towards and beyond the outer edges 9.2 of the contact faces.

For keeping the vibrating element 6 and the counter element 5 easily aligned, the proximal portion of the anchor body e.g. comprises an axial slot 44 or bore, into which a corresponding protrusion 6.4 of the vibrating element fits. For easy slideablility of the suture at least before anchorage, the slot 44 is preferably aligned with the through bore 42 and the distal portion comprises axial grooves 43 extending from the through bore 42 to the slot 44 of the proximal part. For making the anchor body 40 to be suitable for being adapted to be anchored in the most varied tissues (see further below) the anchor body may further comprise per se known barbs 45 in particular on the distal portion. The function of the barbs 45 will be described below.

Anchorage of the suture body 40 and the suture 41 in an opening provided in the tissue in which anchorage is to be provided is effected in substantially the same way as described above, i.e. by liquefaction of the thermoplastic material comprised by the anchor body 40 at its contact face 9, by dislocation of the liquefied material from between the contact faces 8 and 9 and by penetration of the tissue of the opening walls through the liquefied material.

The suture anchor comprising an anchor body 40 according to FIG. 18 can be anchored without adaptation of the method in tissues of the most varied mechanical characteristics, i.e. not only in tissue which has a reduced mechanical strength, but also in tissue which has hardly any pores or cavities to be penetrated by the liquefied material. This is in particular advantageous for anchorage in tissue, whose mechanical and structural characteristics vary relevantly not only locally (e.g. with distance from a tissue surface) but also from one patient to another patient.

If the tissue surrounding the anchor body is of very small mechanical stability, anchorage will be achieved predominantly through the thermoplastic material being liquefied between the contact faces 8 and 9. The liquefied material will easily penetrate the tissue to form a positive-fit connection therewith. At the same time the liquefied material will flow around the suture such that the suture will be fixed relative to the tissue. The barbs of the whole anchor body will not be able to hold the anchor body in the opening and neither the tissue nor the barbs of the proximal section (comprising the liquefiable material) will be able to function as energy directors to cause lateral liquefaction and corresponding anchorage.

If the tissue surrounding the anchor body is of sufficient strength and able to deform the barbs of the proximal section there will be some liquefaction and corresponding anchorage at the lateral surfaces of the proximal body portion and the barbs of the distal body portion may further strengthen the anchorage, however liquefaction between the contact faces and corresponding anchorage will be predominant.

If the tissue surrounding the anchor body is so dense and hard (e.g. corticalis) that none or hardly any of the material which is liquefied between the contact faces is able to penetrate this tissue to form the desired positive-fit connection, the implant will be retained in the opening by the mechanical effect of the barbs and, if the tissue density deeper in the opening is less pronounced, by some lateral anchorage through lateral liquefaction. The suture will be fixed by the material which is liquefied between the contact faces and by the material which is liquefied on the lateral surfaces of the anchor body. This means that anchorage is possible also in very dense tissue without the need of providing cavities therein.

From the above follows that the ability of the suture anchor as illustrated in FIGS. 17 and 18 to exploit not only the anchoring method according to the invention, which provides optimum anchorage in less dense and therefore mechanically weaker tissue, but also purely mechanical anchorage through the barbs, which provide optimum results in very dense and therefore mechanically very strong but hardly porous tissue, results in a very good anchorage quality independent of the mechanical characteristics of the tissue and with a simple bore provided in the tissue.

Instead of the barbs 45, the anchor body may comprise other purely mechanical retention means such as e.g. a thread, with the help of which it will be initially screwed into the tissue. Other retention means such as e.g. parts of a thread or ring-like structures can also be applied. If the suture anchor is to be used in tissue whose mechanical characteristics do not vary in such a large range, the barbs or other retention means may be omitted all together. Furthermore, there may be more than one suture attached to the anchor body 40, wherein the more than one suture may extend through the same through bore 42 in the distal portion of the anchor body or through different such bores (e.g. two bores perpendicular to each other and at different distances from the contact face 9). Furthermore, it is not necessary, that the suture ends are attached to the housing 11 of the vibration source 7 to form a closed load frame. Instead they can be attached to any other stable item which has e.g. a fixed position relative to the tissue.

The suture anchor as described in connection with FIGS. 17 and 18 can be anchored in tissue for other purposes than fixing the suture 41 relative to the tissue. It may e.g. serve for fixing a further element relative to the tissue which further element is then attached to the proximal end of the anchored body 40. In such cases, the suture's only function is the force transmitting function. Therefore, the suture ends can be cut off above the tissue surface after completion of the anchoring process.

It is also possible to not extend the suture 41 right to the housing 11 of the vibration source 7. Instead it could be attached to a support element such as e.g. a plate or ring positioned on an outer tissue surface. Such a support element may be removed after completion of the anchoring process by separating it from the suture ends or it may remain in place, e.g. constituting a support plate or other endoprosthesis part.

FIGS. 19 to 22 show further exemplary embodiments of method and device according to the invention, which embodiments are based on the same principle as the embodiment according to FIGS. 17 and 18. Specific features combined in specific ones of these embodiments can also be combined in different ways, wherein such alternative combinations of features will constitute further exemplary embodiments of the invention.

In the embodiment according to FIG. 19, the anchor body 40 comprises two parts 40' and 40" and a pair of further contact faces 15 and 16 between these two parts, which further contact faces both comprise the liquefiable thermoplastic material. The force transmitting member 41 (e.g. suture, ribbon, wire, cable) is attached to the more proximal one 40" of the parts (more distanced from the contact face of the vibrating element), which for this purpose e.g. comprises the through bore 42. If the liquefiable thermoplastic materials on all concerned contact faces 9, 15 and 16 are the same materials or different material with similar melting temperatures or glass transition temperatures respectively, and liquefaction is desired between the contact faces 8 and 9 as well as between the further contact faces 15 and 16 (two-point anchorage) it will be necessary to equip one of the contact faces 15 or 16 with effective energy directors 46 and design the contact faces 8 and 9 flat. Without such measure liquefaction will occur predominantly between the contact faces 8 and 9.

Obviously, the suture 41 and the inside surface of the bore 42 constitute a further pair of contact faces. However, liquefaction will hardly occur there as hardly any of the vibration energy can be transmitted through the contact faces 8 and 9 and the further contact faces 15 and 16.

The advantage of the two part counter element 5 and the further contact faces 15 and 16 according to FIG. 19 is the fact that they allow a freer selection of location of the anchorage within the opening provided in the tissue.

If the proximal part 40' of the anchor body 40 is made of a non-liquefiable material there will be no liquefaction at the contact faces designated with 8 and 9. This means the proximal part 40' of the anchor body belongs regarding function to the vibrating element 6 (multi-part vibrating element) and serves for transmitting vibration from the vibration source to the further contact faces where liquefaction occurs. Therein, of a longitudinal oscillation available at the contact face 8, only half (directed towards the anchor body, hammer effect) will be able to be transmitted to the proximal part 40' of the anchor body.

The further contact faces 15 and 16 shown in FIG. 19 are not extending perpendicular to the element axes but inclined thereto, wherein one of the contact faces is concave and the other one is convex. Such form of contact faces promotes self centering and holding capability.

FIG. 20 shows a further device according to the invention, which device again comprises a counter element 5 with a two-part anchor body 40 and a suture 41 (or other force transmitting member). The body part 40' in contact with the vibrating element 6 has the form of an O-ring, the body part 40" being positioned more distally comprises a plate on which the suture 41 is attached and a central protrusion adapted to the opening of the O-ring. The vibrating element 6 has a ring-shaped cross section adapted also to the O-ring shaped body part 40'. The protrusion on the distal body part 40" serves for aligning the two parts of the body 40 and the vibrating element 6. The distal body part 40" does not comprise liquefiable thermoplastic material and liquefaction will predominantly occur between the vibrating element 6 and the O-ring, wherein it is the material of the O-ring which is liquefied.

Figure 21:
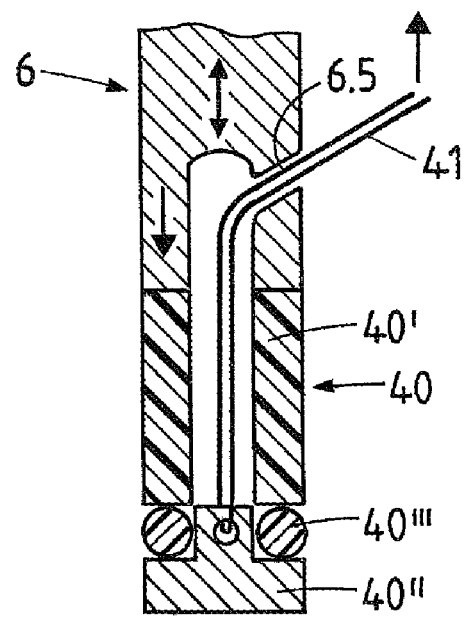

FIG. 21 shows an exemplary embodiment of the device according to the invention similar to the embodiment according to FIG. 20, wherein however the suture 41 (or other force transmitting member) is attached to the central protrusion of the distal body part 40" and reaches through the distal end of the vibrating element 6 to exit for being held at an exit opening 6.5.

Furthermore, the embodiment according to FIG. 21 comprises three body parts: 40', the part adjoining the vibrating element and comprising the contact face 9; 40", the part most distant from the contact face 9; and 40'", the middle part. Therein 40' is tubular and made of the liquefiable thermoplastic material, 40" is made of a non-liquefiable material and the suture 41 is attached to it, and 40'" has the shape of an O-ring and is made also of the liquefiable thermoplastic material.

If all contact faces and further contact faces are about the same regarding material and contact area, liquefaction will predominantly occur between the vibrating element 6 and the body part 40', followed by liquefaction between further contact faces of parts 40' and 40'" and then followed by liquefaction between further contact faces of parts 40'" and 40". If this is not desired, the contact faces need to be different from each other as described further above.

Figure 22:
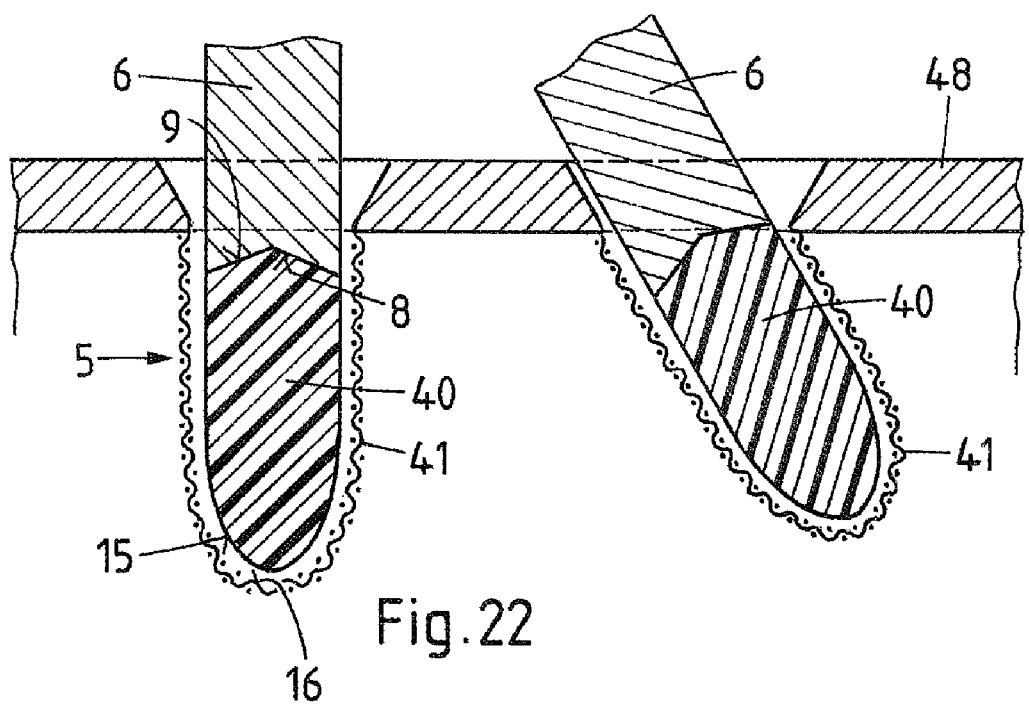
FIG. 22 illustrates a further embodiment of the invention similar to the embodiment according to FIGS. 17 and 18, wherein the suture is replaced by a flexible sleeve.

FIG. 22 shows a further exemplified embodiment of method and device according to the invention in which the counter element 5 comprises an anchor body 40 positioned beyond the distal end of the vibrating element 6 and a flexible force transmitting member 41 reaching past at least the distal end of the vibrating element 6. Therein the flexible force transmitting member is a flexible sleeve made e.g. of a non-liquefiable material, e.g. of metal or PEEK filaments by weaving, braiding, knotting or knitting. This sleeve 41, in addition to its force transmitting function, serves for holding the body 40 in a predetermined position in the opening provided in the tissue and for aligning the body and the vibrating element. The sleeve 41 is preferably attached to a ring- or plate-shaped support element 48 being arranged on an outer tissue surface from which the opening provided in the tissue extends and comprises a through opening adapted to the opening in the tissue. The support element 48 is able to couple the holding force acting on the counter element 5 into a relatively large area of tissue surface which may, as is the case with cortical bone tissue, be of a higher mechanical strength than the underlying tissue (cancellous bone tissue) in which anchorage is to be achieved. The support element 48 may be a support plate as used in osteosynthesis or a resurfacing prosthesis and it may comprise a plurality of through openings and attached or attachable thereto a plurality of sleeves 41.

As indicated in FIG. 17, the sleeves being flexible allow individual orientation of the openings relative to the counter element in a very easy manner.

Obviously, further contact faces 15 and 16 exist between a distal end of the anchor body 40 and the closed distal end of the sleeve 41, where depending on the relation between the contact faces 8 and 9 and the further contact faces 15 and 16 liquefaction may occur also (two-point anchorage).

The invention claimed is:

1. A method for producing an anchorage in a load bearing tissue, the anchorage having a load bearing capability and being created with the aid of mechanical vibration and a thermoplastic material which is liquefiable by the mechanical vibration, the method comprising the steps of:
   providing a vibrating element with a distal end and a proximal end, wherein the proximal end is rigidly attached to a vibration source and the vibrating element is capable of transmitting vibration of the vibration source to the distal end and wherein the distal end comprises a first contact face;
   providing a counter element with a contact end and an opposite end, wherein the contact end comprises a second contact face being adapted to the first contact face to be able to be positioned against the first contact face;
   providing a first liquefiable thermoplastic portion on at least one of the first and second contact faces;
   positioning the vibrating element and the counter element relative to said tissue, while holding the elements against each other with first and second contact faces in contact with each other, and with one of a pair of opposite holding forces being applied to each one of said elements, such that a tissue surface extends across outer edges of the contact faces;
   vibrating the vibrating element while holding the elements against each other and thereby liquefying the liquefiable thermoplastic material between the contact faces;
   maintaining the vibration and the holding forces and thereby moving the elements against each other and letting the liquefied material flow out from between the contact faces for a period of time sufficient for the liquefied material to contact the tissue surface and, on re-solidification, to form a positive fit connection between at least one of the elements and said tissue surface;
   wherein the vibrating element comprises a first axis extending between the distal end and the proximal end and the first contact face extending around the first axis and non-parallel thereto, wherein the counter element comprises a second axis extending between the contact end and the opposite end, and the second contact face extending around the second axis and non-parallel thereto, and wherein in the step of positioning, the first and second axes are aligned and the holding forces or components thereof are directed parallel to the first and second axes;
   wherein the contact face of the vibrating element faces towards the proximal end of the vibrating element and the counter element is positioned between the proximal and the distal end of the vibrating element, the vibrating element reaching past or through the counter element;
   wherein the vibrating element comprises a stem of a smaller cross section and an end piece of a larger cross section and being located at a distal end of the stem and the counter element comprises a through opening or groove adapted to the stem, and wherein the step of positioning comprises positioning the stem through the through opening or into the groove.

2. The method according to claim 1, wherein the liquefaction between the contact faces is enhanced by energy directors provided on one of the contact faces.

3. The method according to claim 1, wherein the holding forces applied to the elements effect substantially no compression parallel to the axes and no lateral enlargement perpendicular to the axes of the vibrating element and the counter element in a solid state.

4. The method according to claim 1, wherein, in the step of positioning, no pressure between the tissue surface in which anchorage is to be achieved and surfaces of the elements in the region of the outer edges of the contact faces is created.

5. The method according to claim 1, wherein the anchorage is produced in an opening of the tissue by positioning the contact faces within the opening.

6. The method according to claim 5, wherein a wall of the opening surrounds the outer edges of the contact faces, the wall being in contact with the elements in the area of the outer edges of the contact faces or having a substantially constant distance therefrom.

7. The method according to claim 1, wherein the counter element comprises a plurality of parts with further contact faces and wherein pairs or further contact faces are positioned against each other, when the vibrating element and the non vibrating element are held against each other.

8. The method according to claim 7, wherein for achieving anchorage in more than one location, at least one further contact face comprises a second liquefiable thermoplastic portion.

9. The method according to claim 1, and further comprising a preliminary step of attaching the distal end of the stem in the end piece by pushing the stem into the end piece or into a depression or bore provided therein and simultaneously vibrating it.

10. The method according to claim 1, wherein the first liquefiable thermoplastic portion is on the second contact face, said end piece comprises a third liquefiable thermoplastic portion at the first contact face and is anchored in the tissue and welded to the counter element.

11. The method according to claim 1, wherein the end piece comprises a fourth liquefiable portion at lateral and/or distal surfaces and wherein the method comprises a preliminary step of anchoring the end piece in the opening provided in the tissue by pressing it against the tissue and vibrating it.

12. The method according to claim 1, wherein the vibrating element comprises a plurality of end pieces fixed to the stem and alternating with counter elements and wherein the steps of positioning, vibrating, maintaining and pulling-out are carried out in succession for each one of the end pieces starting with the most proximal end piece.

13. The method according to claim 1, wherein the counter element or the most proximal counter element respectively comprises a proximal flange with a distal face comprising a fifth liquefiable thermoplastic portion, the vibrating element comprises a shoulder adapted to the flange, and wherein the method comprises a preliminary step of anchoring the flange in a step of the opening provided in the tissue or in an outer tissue surface around the opening provided in the tissue by pressing the flange or head against said outer surface or step while vibrating it.

14. A method attaching a tendon, a ligament or another soft tissue relative to bone tissue, the method comprising the step of anchoring an anchoring element by the method according to claim 1.

15. A method for attaching an endoprosthesis, a suture, a wire, a cable, a ribbon or a plate relative to bone tissue, the method comprising the step of anchoring an anchoring element by the method according to claim 1 in the bone tissue.

16. The method according to claim 10, wherein the third liquefiable thermoplastic material portion is at least in a region in which the distal end of the stem is fixed to the end piece, and wherein the method comprises the further step of pulling the stem out of a bore provided in the end piece and removing the stem from the counter element, after the counter element has been anchored, such that the end piece remains in the tissue and constitutes together with the anchored counter element an implant remaining in the tissue.

* * * * *